US008343052B2

(12) United States Patent
Kawagishi et al.

(10) Patent No.: US 8,343,052 B2
(45) Date of Patent: Jan. 1, 2013

(54) ULTRASONOGRAPH, MEDICAL IMAGE PROCESSING DEVICE, AND MEDICAL IMAGE PROCESSING PROGRAM

(75) Inventors: Tetsuya Kawagishi, Nasushiobara (JP); Yasuhiko Abe, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 594 days.

(21) Appl. No.: 12/302,506

(22) PCT Filed: May 30, 2007

(86) PCT No.: PCT/JP2007/000587
§ 371 (c)(1),
(2), (4) Date: Nov. 26, 2008

(87) PCT Pub. No.: WO2007/138751
PCT Pub. Date: Dec. 6, 2007

(65) Prior Publication Data
US 2009/0198133 A1 Aug. 6, 2009

(30) Foreign Application Priority Data
May 30, 2006 (JP) ................................. 2006-149414

(51) Int. Cl.
*A61B 8/00* (2006.01)
(52) U.S. Cl. .......................... 600/443; 600/407; 600/437
(58) Field of Classification Search .................. 600/407, 600/437, 441, 443; 382/128, 131
See application file for complete search history.

(56) References Cited

U.S. PATENT DOCUMENTS

| 5,785,654 | A | * | 7/1998 | Iinuma et al. | 600/441 |
| 6,053,869 | A | * | 4/2000 | Kawagishi et al. | 600/443 |
| 6,095,978 | A | * | 8/2000 | Takeuchi | 600/443 |
| 6,193,660 | B1 | | 2/2001 | Jackson et al. | |
| 2003/0204139 | A1 | * | 10/2003 | Hashimoto | 600/437 |
| 2004/0064036 | A1 | | 4/2004 | Mao et al. | |

(Continued)

FOREIGN PATENT DOCUMENTS

JP 4-270983 9/1992

(Continued)

OTHER PUBLICATIONS

U.S. Appl. No. 12/540,135, filed Aug. 12, 2009, Ohuchi, et al.
U.S. Appl. No. 12/548,816, filed Aug. 27, 2009, Abe.

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

An ultrasonic diagnostic apparatus capable of measuring a three-dimensional motion of a biological tissue in a short time. An image processor creates volume data based on image data of a B-mode image of a biological tissue and creates image data of a series of tomographic images in time series for the respective two or more sectional positions based on the volume data. A controller displays one tomographic image for each sectional position on a display part. A user operates an operation part to designate a measurement image region on the displayed tomographic image. A displacement calculating part calculates a displacement in time series of the designated measurement image region for each sectional position. A motion information calculating part calculates motion information of the biological tissue based on the displacement of the measurement image region calculated for each sectional position.

19 Claims, 15 Drawing Sheets

U.S. PATENT DOCUMENTS

| | | |
|---|---|---|
| 2004/0081340 A1* | 4/2004 | Hashimoto .................. 382/128 |
| 2005/0096543 A1 | 5/2005 | Jackson et al. |
| 2005/0283079 A1 | 12/2005 | Steen et al. |
| 2006/0058618 A1 | 3/2006 | Nishiura |
| 2007/0038087 A1 | 2/2007 | Abe et al. |
| 2008/0304730 A1 | 12/2008 | Abe |

FOREIGN PATENT DOCUMENTS

| | | |
|---|---|---|
| JP | 2002-140690 | 5/2002 |
| JP | 2004-313291 | 11/2004 |
| JP | 2006-6933 | 1/2006 |
| JP | 2006-61581 | 3/2006 |

* cited by examiner

FIG. 2
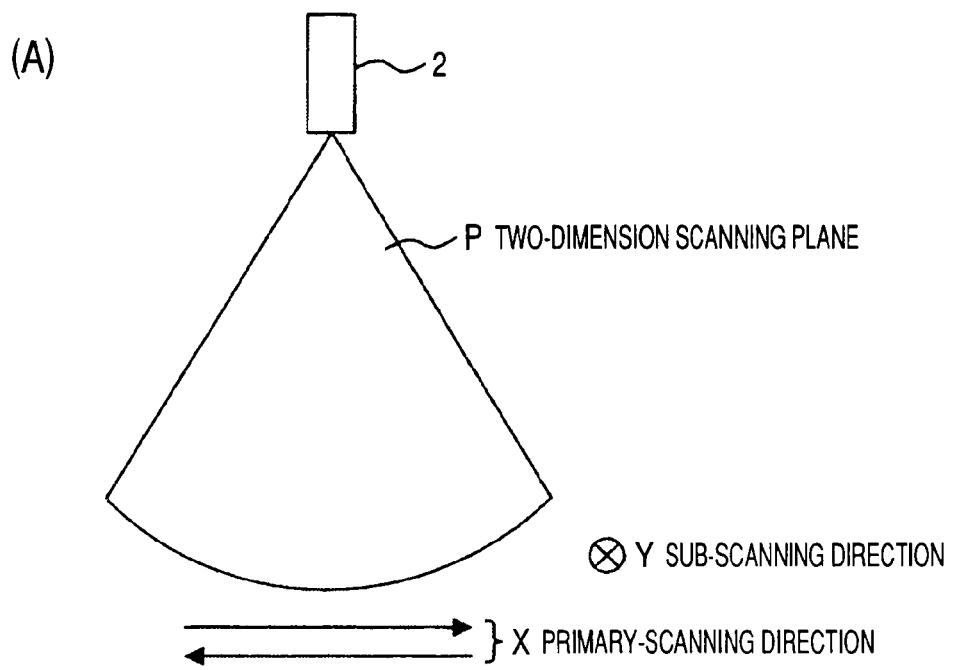
(A)
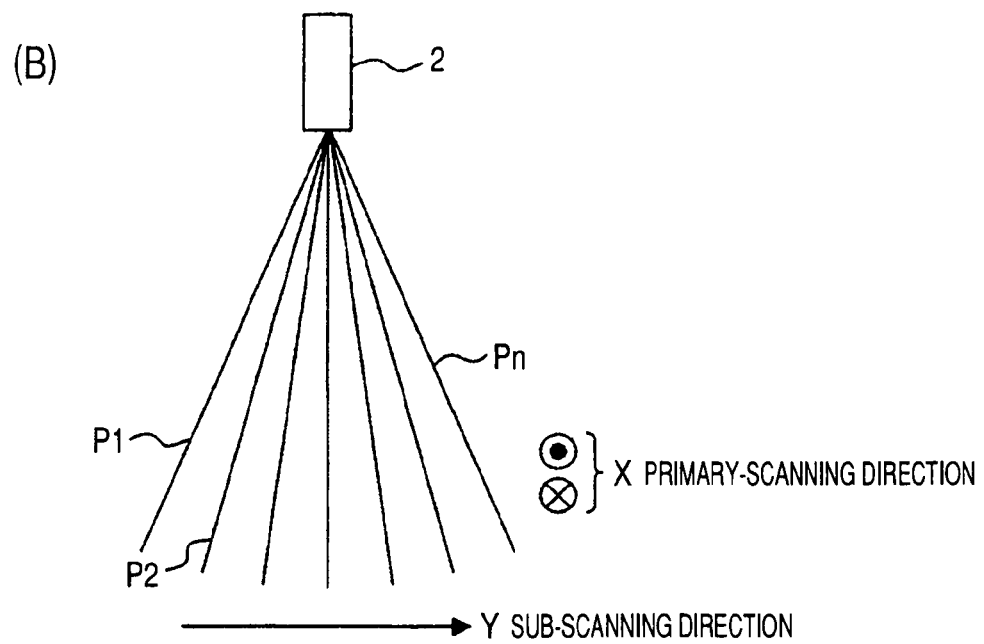
(B)

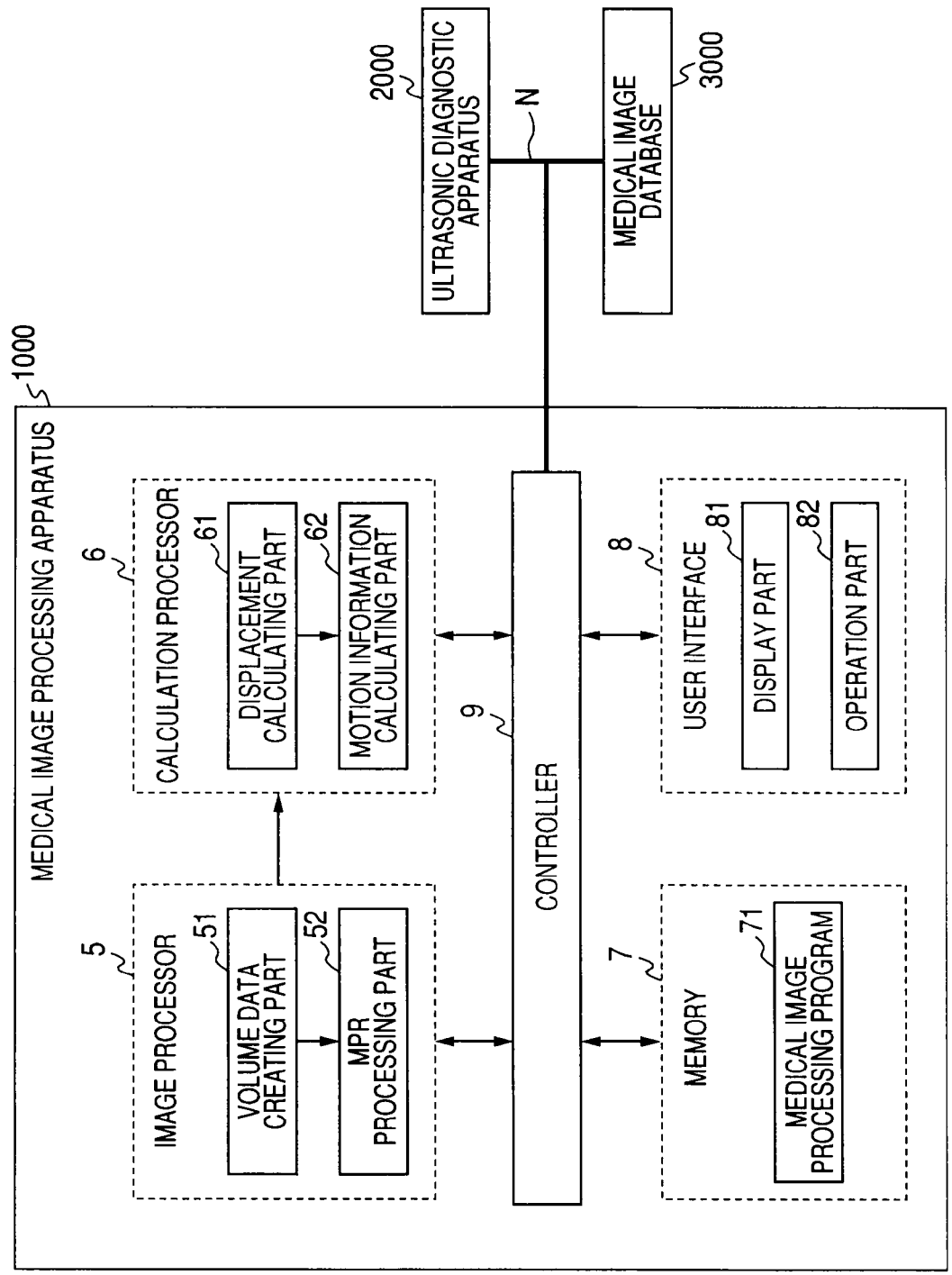

ULTRASONOGRAPH, MEDICAL IMAGE PROCESSING DEVICE, AND MEDICAL IMAGE PROCESSING PROGRAM

TECHNICAL FIELD

The present invention relates to an ultrasonic diagnostic apparatus for transmitting an ultrasonic wave to the inside of an examined body via an ultrasonic probe so as to obtain a medical image of the examined body on the basis of a reflected wave, a medical image processing apparatus and a medical image processing program for processing the medical image obtained by the ultrasonic diagnostic apparatus. Particularly, the present invention relates to an ultrasonic diagnostic apparatus, a medical image processing apparatus and a medical image processing program that are used to estimate a motion function of a biological tissue.

BACKGROUND ART

Since an ultrasonic diagnostic apparatus has a merit such that an image can be observed on site in a simple operation of just bringing an ultrasonic probe into contact with a body surface, the ultrasonic diagnostic apparatus is widely used to examine a function or a shape of the biological tissue. In recent years, estimation of a motion function of a biological tissue such as a motion of a heart wall, and more particularly, estimation of a motion function in three-dimension has been drawing attention.

Patent Document 1 discloses an ultrasonic diagnostic apparatus used to estimate the motion function of the biological tissue. The ultrasonic diagnostic apparatus extracts characteristic points from a two-dimensional image of the biological tissue and designates measurement points on the basis of the characteristic points. Then, a template having a size including a predetermined number or more of characteristic points based on each of the designated measurement points is set, and a cross-correlation process between two images is carried out by using the template to measure a physical parameter such as a displacement or a velocity of the tissue, whereby the measurement precision is increased.

Patent Document: Japanese unexamined patent application publication No. 2004-313291

DISCLOSURE OF THE INVENTION

Problem that the Invention is to Solve

The biological tissue generally moves three-dimensionally. For example, a heart performs a motion in a wall-thickness direction (a variation of the wall thickness, a strain of the wall thickness, and the like) and a motion such as a strain or an expansion/contraction in a direction perpendicular thereto. Since a general motion function estimation is carried out by measuring a velocity or a displacement of the biological tissue in two-dimension, there is a limitation in estimating the three-dimensional motion.

Meanwhile, when the three-dimensional motion is estimated by using a three-dimensional image of the biological tissue, that is, when a plurality of measurement points distributed in three-dimension are designated and a three-dimensional displacement of each of the measurement points is analyzed to estimate the three-dimensional motion of the biological tissue, the amount of data to be processed increases, whereby there arises a problem in that the process time becomes longer.

Additionally, when the motion function estimation is carried out by using the three-dimensional image, a problem arises in that it is difficult to designate a motion measurement target region on the image. For example, when there is a need to measure the variation of the wall thickness of the heart, it is required to find out regions corresponding to an inner lining and an outer lining from the three-dimensional image of the heart and to designate the regions. However, in order to accurately perform such an operation, experienced hand skill and considerable operation time are required.

The present invention is contrived to solve the above-described problems, and an object of the invention is to provide an ultrasonic diagnostic apparatus, a medical image processing apparatus, and an image processing program that make it possible to measure the three-dimensional motion of the biological tissue in a short time.

Additionally, another object of the invention is to provide an ultrasonic diagnostic apparatus, a medical image processing apparatus, and a medical image processing program that make it possible to easily designate a region in which the motion of the biological tissue is measured.

Means for Solving the Problem

In order to achieve the above-described objects, according to a first aspect of the invention, there is provided an ultrasonic diagnostic apparatus including: an ultrasonic probe; a transceiver configured to transmit and receive an ultrasonic wave to and from the ultrasonic probe; an image creating part configured to create image data of a series of tomographic images in time series for each of two or more sectional positions of a biological tissue on the basis of a received signal obtained as a result of transmitting and receiving the ultrasonic wave; a display part configured to display one tomographic image from among the series of tomographic images on the basis of the image data created for each of the two or more sectional positions; a designating part configured to designate a measurement image region on the one displayed tomographic image for each of the two or more sectional positions; and a calculator configured to calculate local motion information showing a motion state of the biological tissue in the designated measurement image region on the basis of the image data of the series of tomographic images for each of the two or more sectional positions and calculate motion information showing the motion state of the biological tissue on the basis of the local motion information calculated for each of the two or more sectional positions, wherein the display part displays the motion information calculated by the calculator.

Further, according to a second aspect of the invention, there is provided an ultrasonic diagnostic apparatus including: an ultrasonic probe; a transceiver configured to transmit and receive an ultrasonic wave to and from the ultrasonic probe; an image creating part configured to create image data of a series of tomographic images in time series for each of one or more sectional positions of a biological tissue on the basis of a received signal obtained as a result of transmitting and receiving the ultrasonic wave; a display part configured to display one tomographic image from among the series of tomographic images on the basis of the created image data for each of the one or more sectional positions; a designating part configured to designate a measurement image region on the one displayed tomographic image for each of the one or more sectional positions; and a calculator configured to calculate local motion information showing a motion state of the biological tissue in the designated measurement image region on the basis of the image data of the series of tomographic images for each of the one or more sectional positions, wherein the display part displays the local motion information calculated by the calculator.

Further, according to a third aspect of the invention, there is provided a medical image processing apparatus configured to process image data of a medical image of a biological tissue obtained by an ultrasonic diagnostic apparatus, the medical image processing apparatus including: a memory configured to store image data of a series of tomographic images in time series at each of two or more sectional positions of the biological tissue; a display part configured to display one tomographic image from among the series of tomographic images on the basis of the image data stored for each of the two or more sectional positions; a designating part configured to designate a measurement image region on the one displayed tomographic image for each of the two or more sectional positions; and a calculator configured to calculate local motion information showing a motion state of the biological tissue in the designated measurement image region on the basis of the image data of the series of tomographic images for each of the two or more sectional positions and calculate motion information showing the motion state of the biological tissue on the basis of the local motion information calculated for each of the two or more sectional positions, wherein the display part displays the motion information calculated by the calculator.

Further, according to a fourth aspect of the invention, there is provided a medical image processing apparatus configured to process image data of a medical image of a biological tissue obtained by an ultrasonic diagnostic apparatus, the medical image processing apparatus including: a memory configured to store image data of a series of tomographic images in time series at each of one or more sectional positions of the biological tissue; a display part configured to display one tomographic image from among the series of tomographic images on the basis of the stored image data for each of the one or more sectional positions; a designating part configured to designate a measurement image region on the one displayed tomographic image for each of the one or more sectional positions; and a calculator configured to calculate local motion information showing a motion state of the biological tissue in the designated measurement image region on the basis of the image data of the series of tomographic images for each of the one or more sectional positions, wherein the display part displays the local motion information calculated by the calculator.

Further, according to a fifth aspect of the invention, there is provided a medical image processing program for causing a computer having a memory configured to store image data of a series of tomographic images in time series at each of two or more sectional positions of a biological tissue and a display to execute the functions of: displaying one tomographic image from among the series of tomographic images on the display on the basis of the stored image data for each of the two or more sectional positions; in response to designation of a measurement region on the one displayed tomographic image, calculating local motion information showing a motion state of the biological tissue in the designated measurement image region on the basis of the image data of the series of tomographic images for each of the two or more sectional positions; calculating motion information showing the motion state of the biological tissue on the basis of the local motion information calculated for each of the two or more sectional positions; and displaying the calculated motion information on the display.

Further, according to a sixth aspect of the invention, there is provided a medical image processing program for causing a computer having memory configured to store image data of a series of tomographic images in time series at each of one or more sectional positions of a biological tissue and a display to execute the functions of: displaying one tomographic image from among the series of tomographic images on the display on the basis of the stored image data for each of the one or more sectional positions; in response to designation of a measurement image region designated on the one displayed tomographic image, calculating local motion information showing a motion state of the biological tissue in the designated measurement image region on the basis of the image data of the series of tomographic images, for each of the one or more sectional positions; and displaying the calculated local motion information on the display.

Advantage of the Invention

In the invention according to the first, third and fifth aspects, one tomographic image is displayed for each of two or more sectional positions of the biological tissue, the local motion information showing the motion state of the biological tissue in the measurement image region is calculated in response to designation of the measurement image region on the displayed tomographic image, the motion information of the biological tissue is calculated on the basis of the calculated local motion information at each of the two or more sectional positions, and the motion information is displayed.

According to this invention, it is possible to measure the three-dimensional motion of the biological tissue by obtaining the motion information based on the local motion information at each of the two or more sectional positions of the biological tissue. Additionally, since the motion information is obtained in consideration of only the local motion information at the two or more sectional positions, it is not necessary to calculate a displacement at a portion between the sectional positions, whereby it is possible to obtain the motion information in a short time.

Further, since the measurement image region is designated on the displayed tomographic image, it is possible to easily designate the measurement image region for obtaining the motion information.

In the invention according to the second, fourth and sixth aspects, one tomographic image is displayed for each of one or more sectional positions of the biological tissue, the local motion information showing the motion state of the biological tissue in the measurement image region is calculated in response to designation of the measurement image region on the displayed tomographic image, and the local motion information is displayed.

According to this invention, since the measurement image region is designated on the displayed tomographic image, it is possible to easily designate the measurement image region for obtaining the local motion information.

BRIEF DESCRIPTION OF THE DRAWINGS

FIG. 2 is a schematic explanatory view showing an example of an aspect of ultrasonic scan of the ultrasonic diagnostic apparatus according to the preferred embodiment of the invention.

FIG. 17 is a schematic block diagram showing an example of an entire configuration of an ultrasonic diagnostic apparatus according to a preferred embodiment of the invention.

DESCRIPTION OF REFERENCE NUMERALS AND SYMBOLS

Figure 1:
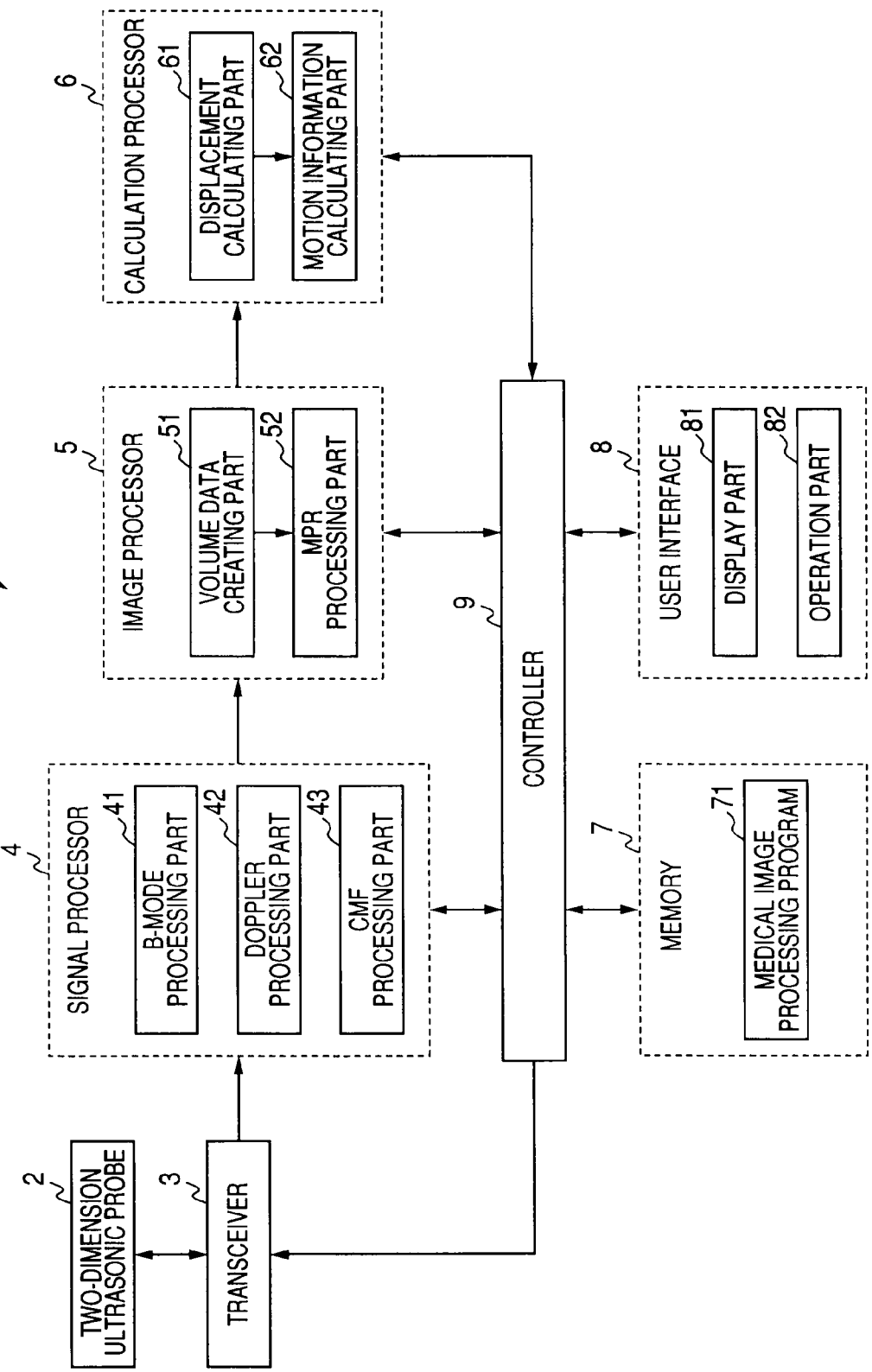
FIG. 1 is a schematic block diagram showing an example of an entire configuration of an ultrasonic diagnostic apparatus according to a preferred embodiment of the invention.

1: Ultrasonic diagnostic apparatus
2: Two-dimension ultrasonic probe
3: Transceiver
4: Signal processor
41: B-mode processing part
5: Image processor
51: Volume data creating part
52: MPR processing part
6: Calculation processor
61: Displacement calculating part
62: Motion information calculating part
7: Memory
71, 72: Medical image processing program
8: User interface
81: Display
82: Operation part
9: Controller
P: Two-dimensional scanning plane
R: Three-dimension scanning plane
X: Primary-scanning direction
Y: Sub-scanning direction
M1 through M6: Inner-lining position image
M1 through M6: Outer-lining position image
1000: Medical image processing apparatus

BEST MODE FOR CARRYING OUT THE INVENTION

An ultrasonic diagnostic apparatus, a medical image processing apparatus, and a medical image processing program according to preferred embodiments of the invention will be described in detail with reference to the accompanying drawings.

<First Embodiment>

An ultrasonic diagnostic apparatus according to an embodiment of the invention will be described. FIG. 1 shows an example of an entire configuration of an ultrasonic diagnostic apparatus according to the invention. An ultrasonic diagnostic apparatus 1 shown in FIG. 1 is an apparatus used to acquire, for example, an image showing a shape of a biological tissue such as a heart or an image showing a bloodstream state, and includes a two-dimension ultrasonic probe 2, a transceiver 3, a signal processor 4, an image processor 5, a calculation processor 6, a memory 7, a user interface 8, and a controller 9. Hereinafter, a detailed example of the respective parts constituting the ultrasonic diagnostic apparatus 1 will be described.

{Memory, User Interface, and Controller}

First, the memory 7, the user interface 8, and the controller 9 will be described. The memory 7 is composed of, for example, a memory device such as a hard disk drive. In the memory 7, a medical image processing program 71 for causing the ultrasonic diagnostic apparatus 1 to execute a characteristic operation according to the invention is stored in advance. Additionally, in the memory 7, various data such as image data of an ultrasonic image and incidental information incidental to the image data (DICOM (Digital Imaging and Communications in Medicine)) are stored.

The user interface 8 is provided with a display part 81 and an operation part 82. The display part 81 corresponds to an example of the "display" according to the invention, and is composed of an arbitrary display device such as a liquid crystal display or a CRT (Cathode Ray Tube) display. The display part 81 displays an image such as an ultrasonic image acquired by the ultrasonic diagnostic apparatus 1, information such as the DICOM incidental information of the image, etc.

The operation part 82 is composed of an arbitrary operation device or input device such as a mouse, a track ball, a joystick, a control panel, and a keyboard.

Particularly, the operation part 82 serves as the "designating part" for designating a measurement image region on an ultrasonic image (tomographic image) displayed on the display part 81. The measurement image region is a region on the tomographic image (in fact, image data corresponding to this region) used as a reference for measuring a motion state of the biological tissue. The ultrasonic diagnostic apparatus 1 operates so as to create a series of volume data in time series by three-dimensionally scanning the biological tissue with the ultrasonic wave and repeating the three-dimension scanning operation, and so as to create the image data of the tomographic image of the biological tissue on the basis of one of the series of volume data, though the detailed contents will be described later. The operation part 82 is used to designate the measurement image region on the tomographic image. The ultrasonic diagnostic apparatus 1 operates so as to measure the motion state of the biological tissue by analyzing how the designated measurement image region varies in time series.

The controller 9 includes a microprocessor such as a CPU, and controls the respective parts of the ultrasonic diagnostic apparatus 1 on the basis of the medical image processing program 71. Particularly, the controller 9 performs a process for displaying an image and a screen on the display part 81. Additionally, the controller performs a process for causing the ultrasonic diagnostic apparatus 1 to execute an operation in response to an operation signal outputted from the operation part 82.

{Two-Dimension Ultrasonic Probe}

As conventional, the two-dimension ultrasonic probe 2 (may be referred to as the ultrasonic probe 2 simply) has a plurality of ultrasonic transducers arranged in two-dimension (for example, in a matrix shape (lattice shape)) (not shown). The plurality of ultrasonic transducers are individually driven by the transceiver 3 described later.

Figure 3:
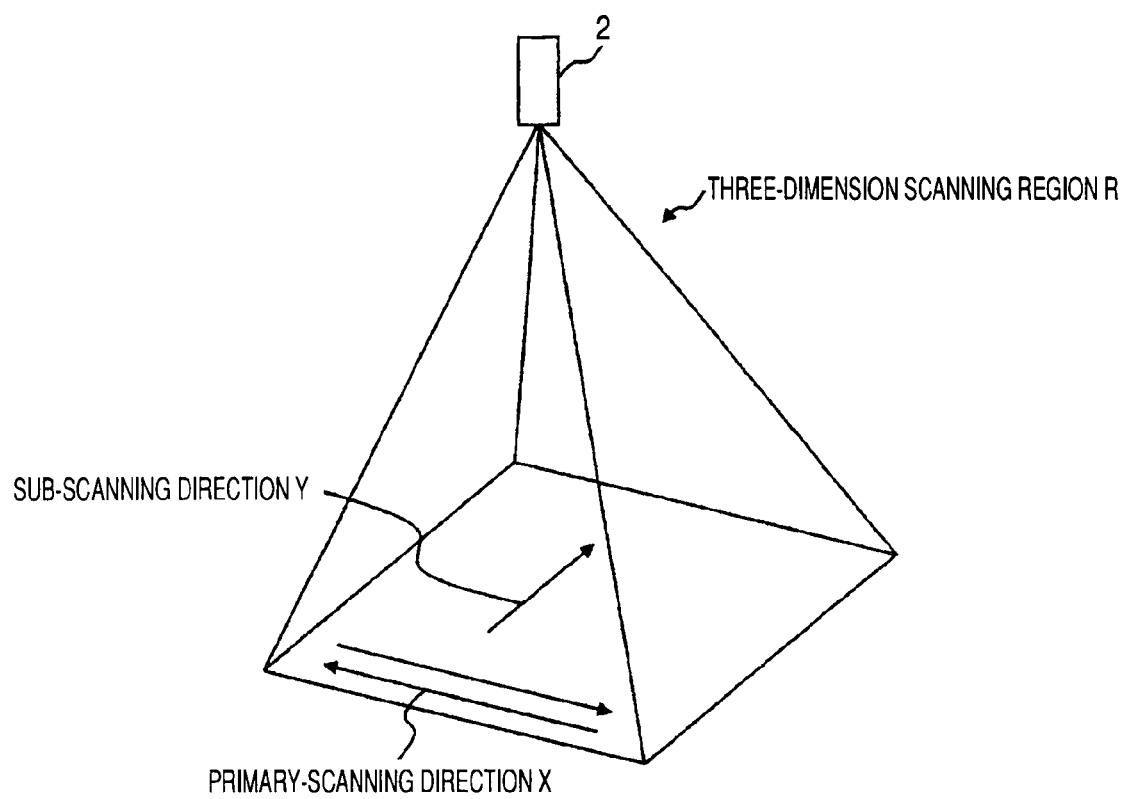
FIG. 3 is a schematic explanatory view showing an example of the aspect of ultrasonic scan of the ultrasonic diagnostic apparatus according to the preferred embodiment of the invention.

FIGS. 2 and 3 show an aspect of ultrasonic wave scanning by the two-dimension ultrasonic probe 2. As shown in FIG. 2A, the ultrasonic probe 2 forms a two-dimensional scanning plane P with a radial shape (fan shape) by scanning with an ultrasonic wave (beam) outputted from an arrangement surface of the ultrasonic transducers in a primary-scanning direction X. Additionally, as shown in FIG. 2B, the ultrasonic probe 2 sequentially forms two-dimensional scanning planes P1. P2, . . . Pn of a fan shape arranged in a sub-scanning direction Y by scanning with the ultrasonic wave in the sub-scanning direction Y perpendicular to the primary-scanning direction X. Accordingly, as shown in FIG. 3, a three-dimension scanning region R is formed.

The sub-scanning direction Y corresponds to "a predetermined direction" according to the invention, and the primary-scanning direction X corresponds to "a direction perpendicular to the predetermined direction." The two-dimensional scanning planes P1 to Pn are formed at "a plurality (n number) of positions along the predetermined direction"

{Transceiver}

The transceiver 3 includes a transmitter for generating an ultrasonic wave by supplying an electric signal to the ultrasonic probe 2 and a receiver for receiving the echo signal (receiving signal) outputted from the ultrasonic probe 2 received a reflected wave of the ultrasonic wave (not shown).

A transmitter of the transceiver 3 includes a clock generating circuit, a transmission delaying circuit, and a pulsar circuit, which are not shown. The clock generating circuit is a circuit for generating a clock signal for determining the transmission timing and the transmission frequency of the ultrasonic wave. The transmission delaying circuit is a circuit that performs a transmission focus by applying a delay at the time of transmission of the ultrasonic wave. The pulsar circuit incorporates a corresponding number of pulsars to individual paths (channels) for the respective ultrasonic transducers, and operates so as to generate a drive pulse at the delayed transmission timing and supply to the respective ultrasonic transducers of the ultrasonic probe 2.

Additionally, a receiver of the transceiver 3 includes a pre-amplifier circuit, an A/D converting circuit, and a receiving delaying/adding circuit, which are not shown. The pre-amplifier circuit amplifies an echo signal outputted from each of the ultrasonic transducers of the ultrasonic probe 2 for each receiving channel. The A/D converting circuit performs an A(analog)/D(digital) conversion of the amplified echo signal. The receiving delaying/adding circuit gives and adds a delay time necessary for determining a receiving directivity to the echo signal having been subjected to the A/D conversion. By the adding process, a reflected component from a direction in accordance with the receiving directivity is emphasized. The signal having been subjected to the adding process may be referred to as "RF data (or raw data)" or the like. The transceiver 3 inputs the acquired RF data to the signal processor 4.

{Signal Processor}

The signal processor 4 performs signal processing for visualizing the amplitude information of the echo signal on the basis of the RF data inputted from the transceiver 3. The data created by the signal processor 4 is sent to the controller 9 to be displayed on the display part 81 of the user interface 8 or to be inputted to the image processor 5. The signal processor 4 mainly includes a B-mode processing part 41, a Doppler processing part 42, and a CMF processing part 43.

(B-Mode Processing Part)

The B(Brightness)-Mode Processor 41 Creates B-Mode Ultrasonic Raster data on the basis of the RF data. More specifically, the B-mode processing part 41 performs a band-pass filter process on the RF data and detects an envelope of the output signal to perform a compression process using a logarithmic transformation on the detected data. Accordingly, image data of a tomographic image in which signal intensity is expressed as a brightness of luminance is created for each of the two-dimensional scanning planes P1 to Pn. The B-mode processing part 41 corresponds to an example of a "first tomographic image creating part" according to the invention.

(Doppler Processing Part)

The Doppler processing part 42 creates the bloodstream information in the biological tissues by, for example, a pulsed Doppler method (PW Doppler method) or a continuous wave Doppler method (CW Doppler method).

In the pulse Doppler method, it is possible to detect an ultrasonic frequency displacement (Doppler displacement frequency component) caused by the Doppler effect of the bloodstream at a certain depth (a distance from the ultrasonic probe 2) by use of a pulse wave. Thus, since the pulse Doppler method has a good distance resolution, the pulse Doppler method is favorably used for the depth measurement of the bloodstream or a tissue of a particular portion. In the application of the pulse Doppler method, the Doppler processing part 42 extracts the Doppler displacement frequency component by phase-detecting a signal in a bloodstream observation region having a specified size from the RF data inputted from the transceiver 3, and performs an FFT (Fast Fourier Transform) process to create data showing the Doppler frequency distribution representing a bloodstream velocity in the bloodstream observation region.

Additionally, unlike the pulse Doppler method, the continuous wave Doppler method uses a continuous wave to obtain a signal in which Doppler displacement frequency components in all sites in a transmission/reception direction of the ultrasonic wave (a diameter direction in the two-dimensional scanning plane P having a fan-shape shown in FIG. 2A) are superimposed, that is, a signal showing all the bloodstream states on the path of the ultrasonic wave. The continuous wave Doppler method has a merit that the measurement velocity is excellent. In the application of the continuous wave Doppler method, the Doppler processing part 42 extracts the Doppler displacement frequency component by phase-detecting a signal received on a sample line for bloodstream observation from the RF data inputted from the transceiver 3 and performs the FFT process, thereby creating data showing the Doppler frequency distribution representing the bloodstream velocity on the sample line.

(CFM Processor)

The CFM (Color Flow Mapping) processor 43 operates at the time of performing a color flow mapping method in which the bloodstream information of the biological tissue is superimposed in colors on a monochrome B-mode image and is displayed in real time. An example of the displayed bloodstream information includes the velocity, distribution, power, etc. of a bloodstream. The bloodstream is obtained as binary information. More specifically, the CFM processor 43 includes a phase-detecting circuit, an MTI (Moving Target Indication) filter, an autocorrelator, a flow-velocity/distribution calculator, and so on. The CFM processor 43 performs a high-pass filter process (MTI filter process) to obtain a morphological signal showing a shape of a biological tissue and a bloodstream signal showing the bloodstream, thereby obtaining the bloodstream information at a plurality of positions, such as the bloodstream velocity, the bloodstream distribution, and the bloodstream power by an autocorrelation process. Additionally, a non-linear process or the like may be carried out in order to reduce the morphological signal.

{Image Processor}

The image processor 5 performs various image processing based on the data created by the signal processor 4. For example, the image processor 5 includes a DSC (Digital Scan Converter), and performs a process of converting data synchronized with the ultrasonic scanning created by the signal processor 4 into data for display (television scanning type data), that is, a scan conversion process.

Additionally, the image processor 5 includes a volume data creating part 51 and an MPR processing part 52 which are described below.

(Volume Data Creating Part)

The volume data creating part 51 performs an interpolation process on the image data of each of the two-dimensional scanning planes P1 to Pn created by the B-mode processing part 41 of the signal processor 4 so as to create volume data (voxel data). The volume data creating part 51 corresponds to an example of a "volume data creating part", and includes, for example, a DSC or a microprocessor.

When a pseudo-three-dimensional image based on the volume data is displayed, the image processor 5 performs a volume rendering process, an MIP (Maximum Intensity Projection) process, etc., on the volume data.

(MPR Processing Part)

The MPR (Multi Plannar Reconstruction) processor 52 performs a section conversion process on the basis of the volume data created by the volume data creating part 51 so as to create image data of a tomographic image at an arbitrary section. The MPR processing part 52 corresponds to an example of a "second tomographic image creating part," and includes, for example, a DSC, a microprocessor, etc. Additionally, the MPR processing part 52, the volume data creating part 51, and the B-mode processing part 41 of the signal processor 4 serve as an example of the "image creating part" according to the invention.

{Calculation Processor}

The calculation processor 6 is used to calculate local motion information showing a local motion state or motion information showing a broader motion state of the biological tissue on the basis of the image data of the tomographic image created by the MPR processing part 52 of the image processor 5, and serves as an example of the "calculator" according to the invention.

For example, when the biological tissue is a heart, an example of the local motion information obtained by the calculation processor 6 includes variation in thickness of a heart wall, a velocity of the variation, a motion strain of the heart wall, a strain rate, a rotary angle of an inner lining or an outer lining of the heart wall, a velocity of the rotary angle (rotary velocity), a relative rotary angle of the inner lining or the outer lining, and the like (the detailed contents will be described later).

Additionally, an example of the motion information includes, for example, a straining motion of the heart wall, a velocity of the straining motion, expansion/contraction (shortening), a velocity of the expansion/contraction, a strain of the motion of the heart wall, a strain rate, a relative rotary gradient, and the like (the detailed contents will be described below).

The calculation processor 6 includes a microprocessor such as a CPU. The calculation processor 6 is provided with a displacement calculating part 61 and a motion information calculating part 62.

(Displacement Calculating Part)

The displacement calculating part 61 tracks the measurement image region designated on the tomographic image by the operation part 82 in time series so as to calculate the displacement (of the biological tissue) in time series of the measurement image region. The displacement of the measurement image region corresponds to an example of "local motion information" according to the invention.

It is possible to obtain a displacement velocity by dividing the displacement between the two-dimensional and three-dimensional images in time series at a time interval (frame interval) between the images. On the contrary, it is possible to obtain the displacement between the images by multiplying the displacement velocity of the measurement image region by the time interval between the images. That is, when the time interval between the images is given, it is possible to suppose that the displacement and the velocity are synonymous with each other. For this meaning, the displacement and the velocity may be considered to be identical with each other in the invention.

An operation of the displacement calculating part 61 will be described in more detail. As described above, the ultrasonic diagnostic apparatus 1 creates the series of volume data of the biological tissue in time series, and creates the image data of the tomographic image based on one of the volume data (volume data at a certain time (time phase)). Then, the measurement image region is designated on the tomographic image. The displacement calculating part 61 tracks how much the measurement image region is displaced in the volume data at a different time (time phase) in time series. Thus, the process for tracking the displacement of the measurement image region in the volume data in time series may be referred to as "three-dimensional tracking."

Additionally, the displacement calculating part 61 is capable of tracking how much the measurement image region designated on the tomographic image is displaced in time series in the tomographic image at a different time (time phase) at the same sectional position as that of the tomographic image. Such a tracking process may be referred to as "two-dimensional tracking." The two-dimensional tracking is carried out in such a manner that the image data of the tomographic image in time series at the sectional position is created on the basis of the volume data in time series and the displacement in the image data of the tomographic image in time series is tracked. Additionally, the two-dimensional tracking may be carried out by tracking the displacement at the sectional position of the volume data in time series.

Such a tracking process may be carried out by the known method. For example, in the same manner as the method disclosed in the above-described Patent Document 1, the two-dimensional tracking may be carried out in such a manner that characteristic points are extracted from the respective measurement image regions designated on a plurality of tomographic images in time series and a measurement point is designated on the basis of the characteristic points. Then, a template having a size including a predetermined number or more of characteristic points on the basis of the measurement point is set, and a correlation process (pattern matching process) of two tomographic images (measurement image region) is carried out by using the template, whereby calculation of the displacement for each measurement point is carried out.

Further, in the three-dimensional tracking, in a similar manner, a three-dimensional template is set on the basis of the volume data, and a pattern matching process on two volume data at different times (time phases) is carried out by using the three-dimensional template to calculate the displacement at each measurement point.

Additionally, the characteristic point and the measurement point may be designated in only the measurement image region (for example, an inner-lining position image m1 described below and shown in FIG. 5), or may be designated in a region other than the measurement image region, such as a region between the boundaries of the measurement image regions (for example, an image region corresponding to a section of a heart wall surrounded by the inner-lining position image m1 and an outer-lining position image M1) and a region in the vicinity of the measurement image region. In any case, it is possible to apply an arbitrary tracking method by which it is possible to calculate the displacement in time series of the designated measurement image region.

The displacement of the measurement points obtained by the two-dimensional tracking or the three-dimensional tracking can be directly used as the displacement of the measurement image region. Additionally, it is possible to calculate the displacement of the boundary of the measurement image region (for example, inner-lining position images m1 to m3 or outer-lining position images M1 to M3 described below and shown in FIG. 6) on the basis of the displacement of the measurement points, and use the displacement of the boundary as the displacement of the measurement image region.

Thus, the displacement calculating part 61 designates a plurality of measurement points in a measurement image region designated in one tomographic image, and obtains the positions of the measurement points, respectively, for a tomographic image in each frame. Then, the displacement calculating part calculates the displacement in time series of each of the measurement points on the basis of the positions of the measurement points for the tomographic image in each frame, and calculates the displacement of the designated measurement image region on the basis of the displacement of the measurement points.

(Motion Information Calculating Part)

The motion information calculating part 62 performs a process for calculating motion information showing a (broader) motion state of a biological tissue on the basis of the displacement of the measurement image region calculated by the displacement calculating part 61. A detailed example of the process for calculating the motion information by the motion information calculating part 62 will be described later.

[Operation Aspect]

An example of the operation aspect of the ultrasonic diagnostic apparatus 1 with the above-described configuration according to this embodiment will be described with reference to FIGS. 4 to 14. Here, a case will be described in which a heart motion state is evaluated. Hereinafter, an ultrasonic image acquiring operation and a measurement image region designating operation will be described with reference to FIGS. 4 to 6, and then a measurement image region tracking process and a motion information calculating process will be described with reference to FIGS. 7 to 14.

{Acquisition of Ultrasonic Image and Designation of Measurement Image Region}

First, an ultrasonic image of a heart as a target for evaluating a motion state is acquired. For this acquisition, when a predetermined operation is carried out in a state where the ultrasonic probe is placed on a body surface in the vicinity of the heart of the examined person (in general, in the vicinity of an apex portion of the heart), the transceiver 3 controls the ultrasonic probe 2 on the basis of the control of the controller 9 so that the three-dimensional ultrasonic scanning of the heart (ultrasonic scanning shown in FIGS. 2 and 3) is carried out (S01).

The ultrasonic diagnostic apparatus 1 repeatedly performs the three-dimensional ultrasonic scanning. At this moment, it is desirable that the three-dimensional ultrasonic scanning is repeatedly carried out for a time not less than one cardiac cycle (one period of a heartbeat, for example, from a current R wave to a subsequent R wave in an electrocardiogram).

Next, the transceiver 3 converts echo signals sequentially outputted from the ultrasonic probe 2 into RF data and sequentially inputs to the signal processor 4. The B-mode processing part 41 of the signal processor 4 sequentially creates image data of a tomographic image in each of the two-dimensional scanning planes P1 to Pn on the basis of the RF data (S02). The created image data is inputted to the image processor 5. When volume data is obtained in advance, the image data of the tomographic image may be created by executing the MPR processing part the like on the volume data.

Subsequently, the volume data creating part 51 of the image processor 5 sequentially executes an interpolation process on the image data of the tomographic images in the two-dimensional scanning planes P1 to Pn, and sequentially creates volume data in a three-dimension scanning region R corresponding to one three-dimensional ultrasonic scanning (S03). Thus, a plurality of volume data in time series are obtained.

Next, the MPR processing part 52 creates image data of a tomographic image at a predetermined sectional position of the heart on the basis of one of the plurality of generated volume data. In this embodiment, image data of an apical four chamber image (may be referred to as an apical four chamber tomogram) and image data of an apical two chamber image (maybe referred to as an apical two chamber tomogram) are created (S04). Here, the apical four chamber image and the apical two chamber image each corresponds to a sectional image at a sectional position along a longitudinal direction of the heart, and their sectional positions are orthogonal to each other.

The controller 9 controls the display part 81 to display the tomographic images (the apical four chamber image and the apical two chamber image) based on the image data created in Step S04 (S05). FIG. 5 shows an example of a display aspect at this moment. In FIG. 5, the display part 81 (a display screen thereof) is provided with sectional-position designating image displays 81A and 81B based on the image data created in Step S04. In FIG. 1, the apical four chamber image is displayed on the sectional-position designating image display part 81A and the apical two chamber image is displayed on the sectional-position designating image display part 81B.

Additionally, in the case of ultrasonic diagnosis by electrocardiogram synchronization, an electrocardiogram is displayed on an electrocardiogram display portion 81F of the display part 81. A time cursor T showing a time (time phase and time) at which the tomographic images displayed on the sectional-position designating image displays 81A and 81B are acquired is displayed on the electrocardiogram display portion 81F. In FIG. 5, the time cursor T is located at a time phase of the R-wave in the electrocardiogram. Here, it is possible to configure so that the time cursor T can be moved (e.g., dragged and dropped) in a time direction (horizontal direction) of the electrocardiogram and so that a tomographic image at a destination time (time phase) of the time cursor T is created from the volume data and displayed on the sectional-position designating image displays 81A and 81B.

Sectional-position designating cursors C1, C2 and C3 are disposed at horizontal positions on the sectional-position designating image display part 81B. For example, while observing the apical four chamber image or the apical two chamber image, a user operates a mouse of the operation part 82 to drag and drop the sectional-position designating cursors C1 to C3 in a vertical direction (a longitudinal direction of the heart), thereby designating a sectional position (S06).

The controller 9 determines the coordinate of the designated sectional position on the image data of the apical four chamber image on the basis of, for example, the coordinate in the display screen of the apical four chamber image (and/or the apical two chamber image) and the coordinate in the display screen of the sectional-position designating cursors C1 to C3, and sends it to the image processor 5

The MPR processing part 52 creates image data of a tomographic image having a section in the short-axis direction of the heart at each of the designated sectional positions, on the basis of the coordinate information sent from the controller 9 and the plurality of volume data created in Step S03 (S07). At this moment, the MPR processing part 52 creates the image data of the tomographic image at each of the designated sectional positions for each of the plurality of volume data.

The controller 9 controls tomographic image display portions 81C, 81D and 81E of the display part 81 to display tomographic images on the basis of the image data created from the same volume data as created in Step S04, from among the image data created in Step S07 (S08). In Step S07, the image data involved with the display process in Step S08 is first created, and the creation process of the other image data may be carried out in the background after the process in Step S08.

Figure 5:
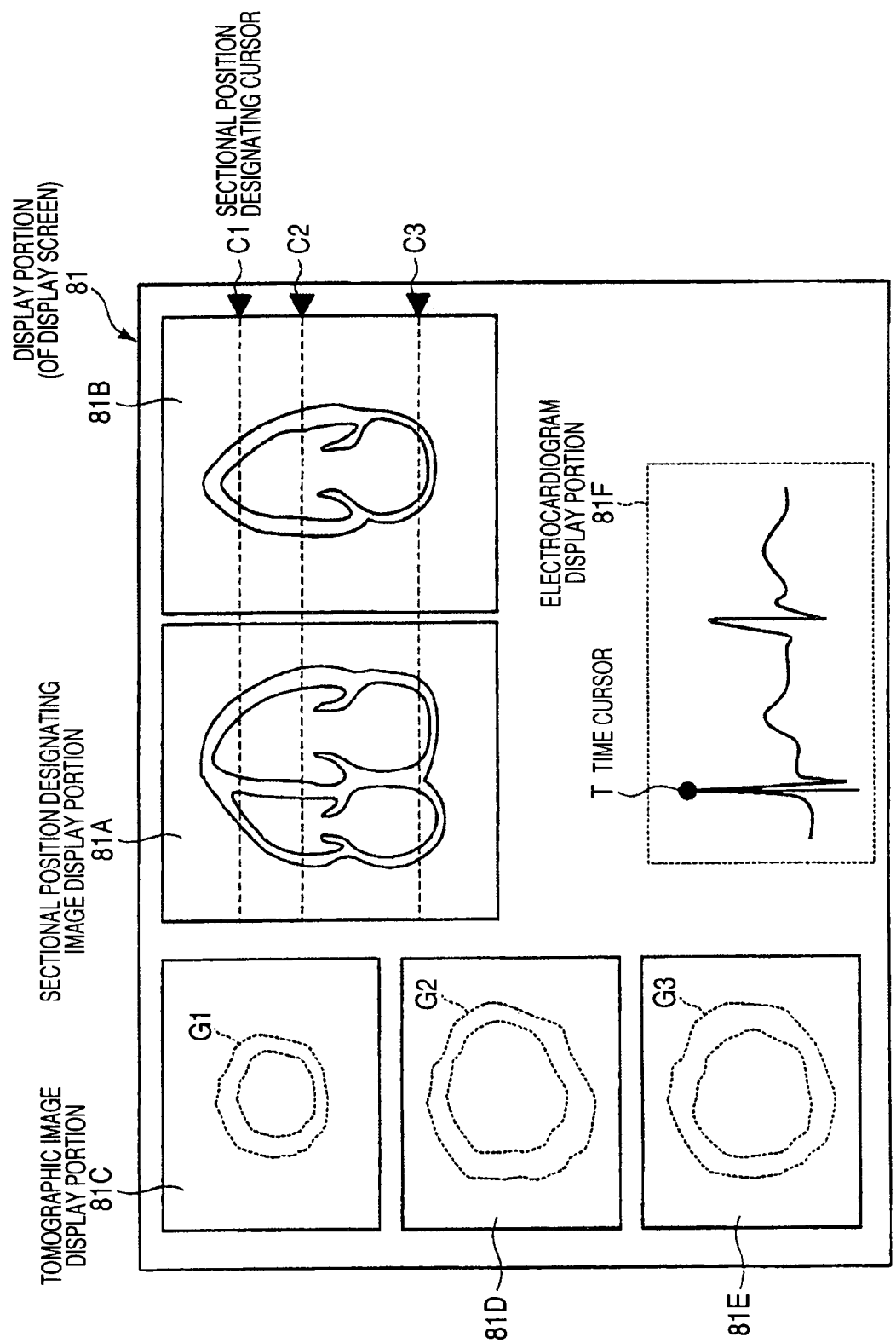
FIG. 5 is a schematic view showing an example of a display aspect of a display screen of the ultrasonic diagnostic apparatus according to the preferred embodiment of the invention.

In the example shown in FIG. 5, the sectional-position designating cursors C1 to C3 are respectively set to an apex-portion level, a papillary-muscle level, and a base-portion level of the heart. In this case, a tomographic image of the apex-portion level (an apex portion short-axis image G1) designated with the sectional-position designating cursor C1 is displayed on the tomographic image display portion 81C. Additionally, a tomographic image of the papillary-muscle level (a papillary muscle short-axis image G2) designated with the sectional-position designating cursor C2 is displayed on the tomographic image display portion 81D. Additionally, a tomographic image of the base-portion level (a base portion short-axis image G3) designated with the sectional-position designating cursor C3 is displayed on the tomographic image display portion 81E.

The user operates the operation part 82 to designate the measurement image region on the tomographic image displayed on each of the tomographic image display portions 81C, 81D and 81E (S09). This operation is carried out, for example, by dragging a mouse to input a boundary showing the measurement image region onto the tomographic image.

Figure 6:
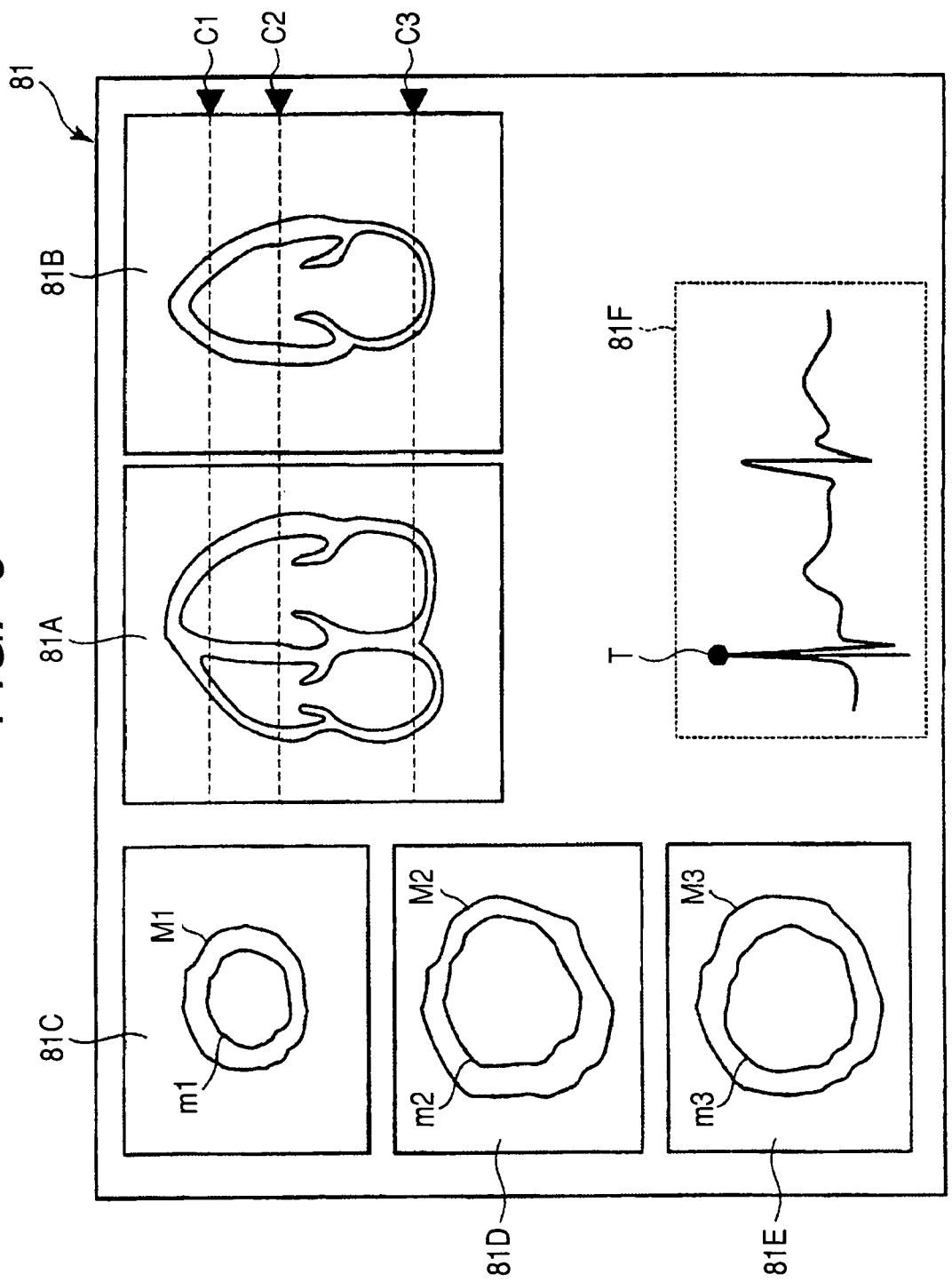
FIG. 6 is a schematic view showing an example of the display aspect of the display screen of the ultrasonic diagnostic apparatus according to the preferred embodiment of the invention.

FIG. 6 shows an example of an aspect of designating the measurement image region on the apex portion short-axis image G1, the papillary muscle short-axis image G2 and the base portion short-axis image G3 shown in FIG. 5. The dashed line shown inside of each of the short-axis images G1 to G3 indicates the inner lining, while the dashed line shown outside indicates the outer lining. While observing the displayed short-axis images G1 to G3, the user operates the operation part 82 to trace the inner lining and the outer lining, thereby inputting a line showing the measurement image region.

Thus, as shown in FIG. 6, in the apex portion short-axis image G1, an inner-lining position image m1 obtained by tracing the inner lining of the heart wall and an outer-lining position image M1 obtained by tracing the outer lining are inputted. Additionally, in the papillary muscle short-axis image G2, an inner-lining position image m2 obtained by tracing the inner lining of the heart wall and an outer-lining position image M2 obtained by tracing the outer lining are inputted. Additionally, in the base portion short-axis image G3, an inner-lining position image m3 obtained by tracing the inner lining of the heart wall and an outer-lining position image M3 obtained by tracing the outer lining are inputted.

Consequently, the ultrasonic image acquiring operation and the measurement image region designating operation end.

{Measurement Image Region Tracking Process and Motion Information Calculating Process}

Next, the measurement image region tracking process (displacement calculating process) and the motion information calculating process will be described with reference to FIGS. 7 to 14. Hereinafter, description will be made for each of the motion information to be acquired. Each process described below is carried out following Step S09 of the flowchart shown in FIG. 4. A plurality of processes described below may be sequentially carried out or may be carried out in parallel. Moreover, it is not necessary to individually perform the same process carried out in the different processes.

(Motion Information: Straining Motion)

First, a process of acquiring a straining motion state of a heart wall as motion information will be described with reference to FIGS. 7 and 8. When the measurement image region is designated on the tomographic image displayed on each of the tomographic image display portions 81C, 81D and 81E (S09), the displacement calculating part 61 performs the two-dimensional tracking of the inner-lining position image m1 based on the image data of the tomographic image created for each of the plurality of volume data in time series (S07), thereby calculating a rotary angle (local motion information) of the inner-lining position image m1 about an axis in a direction orthogonal to the section of the apex portion short-axis image G1 (a longitudinal direction of the heart). In a like manner, in the papillary muscle short-axis image G2 and the base portion short-axis image G3, the displacement calculating part calculates rotary angles (local motion information) of the inner-lining position images m2 and m3 about the axis in the longitudinal direction of the heart (S11). Instead of the inner-lining position images m1, m2 and m3, rotary angles of the outer-lining position images M1, M2 and M3 may be calculated.

At this moment, the displacement calculating part 61, for example, calculates the rotary angles of the inner-lining position images m1, m2 and m3 for each time phase as the rotary angles at the time phase (reference time phase) at which the inner-lining position image m1 etc. are inputted in Step S09. The displacement calculating part may sequentially calculate the rotary angles of the inner-lining position images m1, m2 and m3 in the adjacent frames (that is, continuous frames) in time series.

The motion information calculating part 62 calculates a difference (a relative rotary angle) between the rotary angle of the inner-lining position image m1 and the rotary angle of the inner-lining position image m2 (S12). In the same manner, the motion information calculating part calculates a difference (a relative rotary angle) between the rotary angle of the inner-lining position image m2 and the inner-lining position image m3 (S13). The relative rotary angle corresponds to an example of "difference information" according to the invention.

The processes shown in Step S12 and S13 will be described in detail with reference to FIG. 8. In the tomographic image display portions 81C, 81D and 81E, for example, a counter-clockwise direction is defined as a normal rotary direction (+θ direction). Additionally, a rotary angle of the inner-lining position image m1 is denoted by θ1, a rotary angle of the inner-lining position image m2 is denoted by θ2, and a rotary angle of the inner-lining position image m3 is denoted by θ3.

At this moment, a relative rotary angle $\Delta\theta12$ calculated in Step S12 is obtained by $\Delta\theta12=\theta1-\theta2$ (or $\theta2-\theta1$). Additionally, a relative rotary angle $\Delta\theta23$ calculated in Step S13 is obtained by $\Delta\theta23=\theta2-\theta3$ (or $\theta3-\theta2$).

The relative rotary angle $\Delta\theta12$ obtained in Step S12 is information showing a straining motion state (magnitude) of the heart wall between the sectional positions of the apex portion short-axis image G1 and the papillary muscle short-axis image G2. That is, when the relative rotary angle $\Delta\theta12=0$ ($\theta1=\theta2$), it is possible to suppose that, at an arbitrary position between the sectional positions, the heart wall rotates by the same angle in the same direction and there is no strain in the rotary direction.

Meanwhile, in the case of $|\Delta\theta12|\neq0$, there is a difference in rotary angle between the sectional positions, and the heart wall is strained in the rotary angle direction. The strain of the heart wall is larger as the absolute value of the relative rotary angle $\Delta\theta12$ is larger. For example, when the signs of the θ1 and θ2 are different from each other, that is, when the rotary direction of the inner-lining position image m1 and the rotary direction of the inner-lining position image m2 are opposite to each other, the absolute value of the relative rotary angle $\Delta\theta12$ is comparatively larger.

In the same manner, the relative rotary angle $\Delta\theta23$ obtained in Step S13 is information showing the magnitude of a straining motion of the heart wall between the sectional positions of the papillary muscle short-axis image G2 and the base portion short-axis image G3.

The controller 9 controls the display part 81 to display the relative rotary angles $\Delta\theta12$ and $\Delta\theta23$ calculated in Steps S12 and S13 as the motion information showing the magnitude of a straining motion of the heart wall (S14). The user can grasp the magnitude of the straining motion of the heart wall by referring to the displayed relative rotary angles $\Delta\theta12$ and $\Delta\theta23$. Here, it is also possible to calculate the relative rotary angles of the inner lining and the outer lining of the heart wall, respectively, and evaluate the magnitude of the straining motion on the basis of the two relative rotary angles (for example, by obtaining an average of the two relative rotary angles).

By differentiating the relative rotary angle $\Delta\theta12$ by time, it is possible to obtain the velocity of a straining motion of the heart wall between the inner-lining position images m1 and m2. In the same manner, by differentiating the relative rotary angle $\Delta\theta23$ by time, it is possible to obtain the velocity of a straining motion of the heart wall between the inner-lining position images m2 and m3. Then, it is possible to configure so as to display the velocities on the display part 81. Here, "differentiation" includes a process of dividing the relative rotary angle by a time interval between the frames where the relative rotary angles are obtained, as well as a general differentiation calculation.

(Motion Information: Relative Rotary Gradient)

A process of acquiring a relative rotary gradient of the heart wall as the motion information will be described with reference to FIGS. 9 and 10. The relative rotary gradient is information showing the degree of a straining motion of the heart wall.

Figure 7:
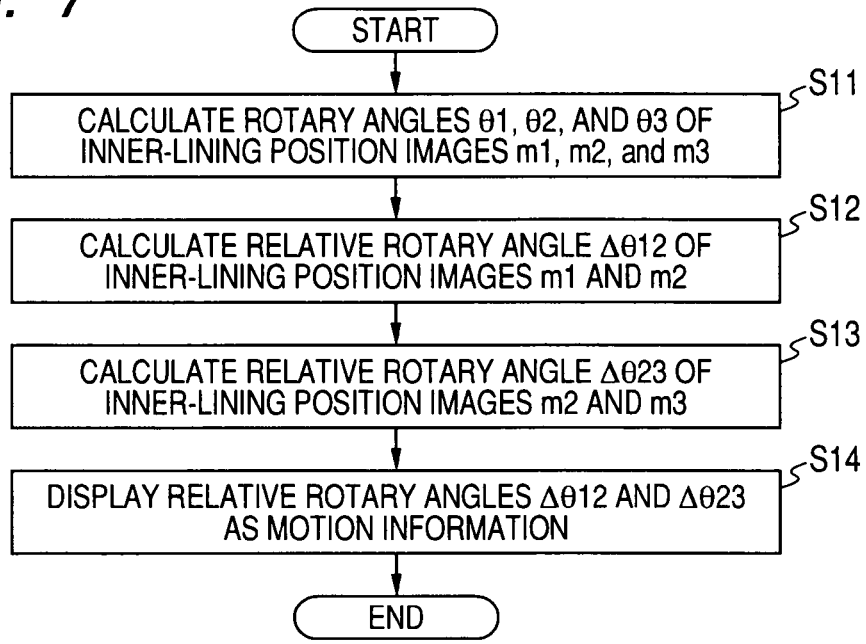
FIG. 7 is a flowchart showing an example of a process of the ultrasonic diagnostic apparatus according to the preferred embodiment of the invention.
Figure 8:
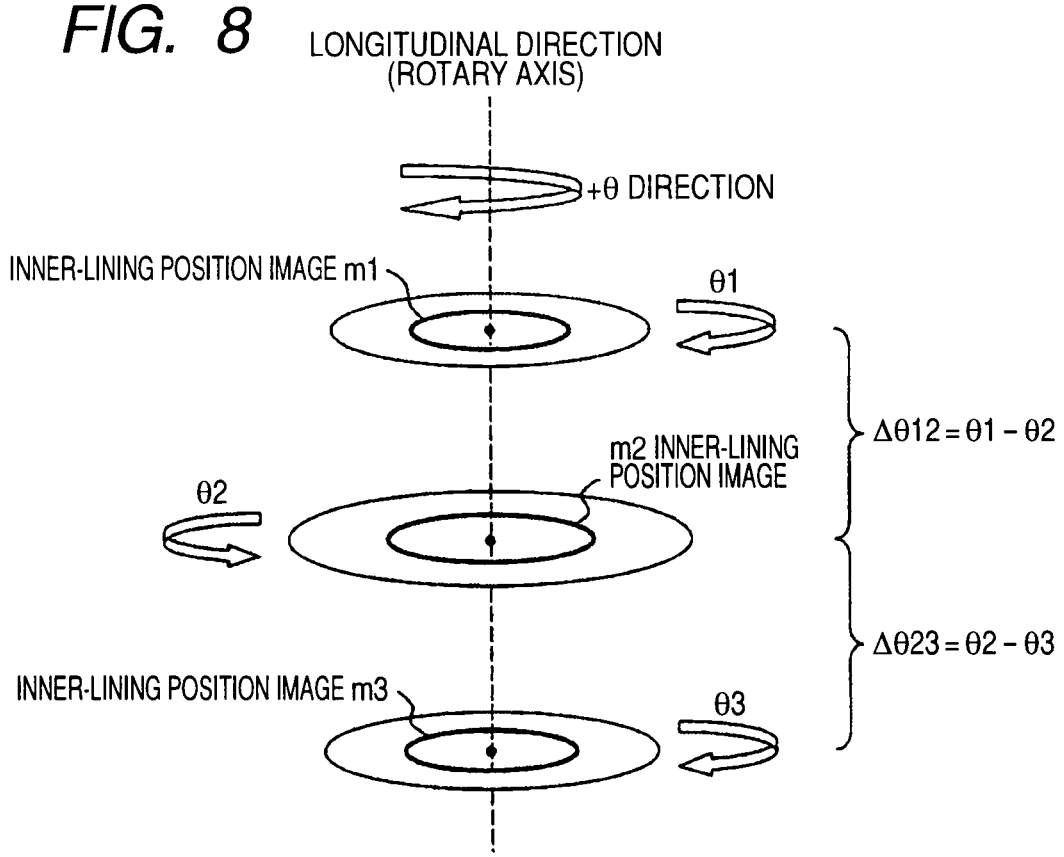
FIG. 8 is a schematic explanatory view showing the process of the ultrasonic diagnostic apparatus according to the preferred embodiment of the invention.

First, in the same manner as in Step S1 shown in FIG. 7, the displacement calculating part 61 calculates the rotary angle θ1 of the inner-lining position image m1 of the apex portion short-axis image G1, the rotary angle θ2 of the inner-lining position image m2 of the papillary muscle short-axis image G2, and the rotary angle θ3 of the inner-lining position image m3 of the base portion short-axis image G3 (S21).

Next, in the same manner as in Steps S12 and S13, the motion information calculating part 62 calculates the relative rotary angle $\Delta\theta12$ between the rotary angle θ1 of the inner-lining position image m1 and the rotary angle θ2 of the inner-lining position image m2 (S22), and calculates the relative rotary angle $\Delta\theta23$ between the rotary angle θ2 of the inner-lining position image m2 and the rotary angle θ3 of the inner-lining position image m3 (S23).

Subsequently, the motion information calculating part 62 calculates a distance d12 between the apex portion short-axis image G1 and the papillary muscle short-axis image G2 (S24), and calculates a distance d23 between the papillary muscle short-axis image G2 and the base portion short-axis image G3 (S25). The distances d12 and d23 can be calculated, for example, on the basis of the coordinates of the sectional positions of the apex portion short-axis image G1, the papillary muscle short-axis image G2, and the base portion short-axis image G3 obtained by the controller 9 following Step S06.

Figure 10:
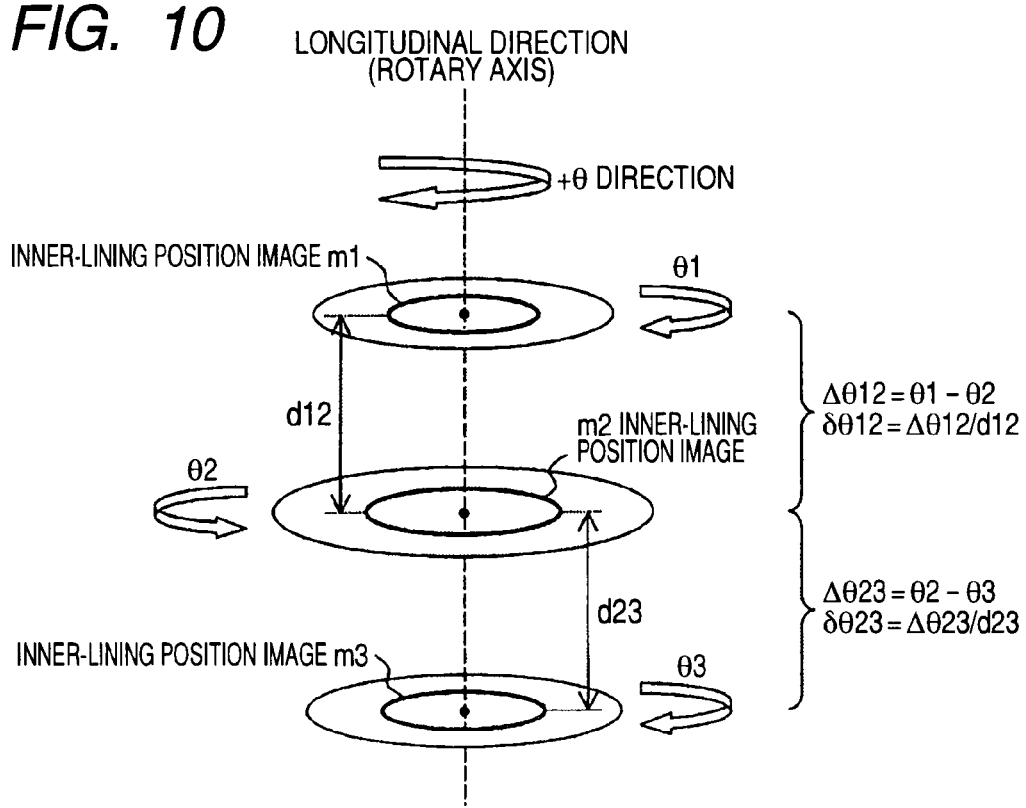
FIG. 10 is a schematic explanatory view showing the process of the ultrasonic diagnostic apparatus according to the preferred embodiment of the invention.

Additionally, as shown in FIG. 10, the motion information calculating part 62 divides the relative rotary angle $\Delta\theta12$ obtained in Step S22 by the distance d12 obtained in Step S24 to calculate the relative rotary gradient $\delta\theta12=\Delta\theta12/d12$ between the inner-lining position image m1 and the inner-lining position image m2 (S26). Similarly, the motion information calculating part 62 divides the relative rotary angle $\Delta\theta23$ obtained in Step S23 by the distance d23 obtained in Step S25 to calculate the relative rotary gradient $\delta\theta23=\Delta\theta23/d23$ between the inner-lining position image m2 and the inner-lining position image m3 (S27).

The controller 9 controls the display part 81 to display the relative rotary gradients $\delta\theta12$ and $\delta\theta23$ calculated in Steps S26 and S27 as the motion information showing the degree of a straining motion of the heart wall (S28).

The relative rotary gradient $\delta\theta12$ shows the magnitude of strain per unit distance between the inner linings at the apex-portion level and the papillary-muscle level. Additionally, the relative rotary gradient $\delta\theta23$ shows the magnitude of strain per unit distance between the inner linings at the papillary-muscle level and the base-portion level. That is, the relative rotary gradients $\delta\theta12$ and $\delta\theta23$ are motion information showing the degree of strain of the heart wall (inner lining). The user can grasp the degree of a straining motion of the heart wall by referring to the displayed relative rotary gradients $\delta\theta12$ and $\delta\theta23$. It is also possible to calculate the relative rotary gradients for the inner lining and the outer lining of the heart wall, and evaluate the degree of a straining motion on the basis of the two relative rotary gradients (for example, by obtaining an average from the two relative rotary gradients).

(Motion Information: Longitudinal Expansion-Contraction)

Figure 11:
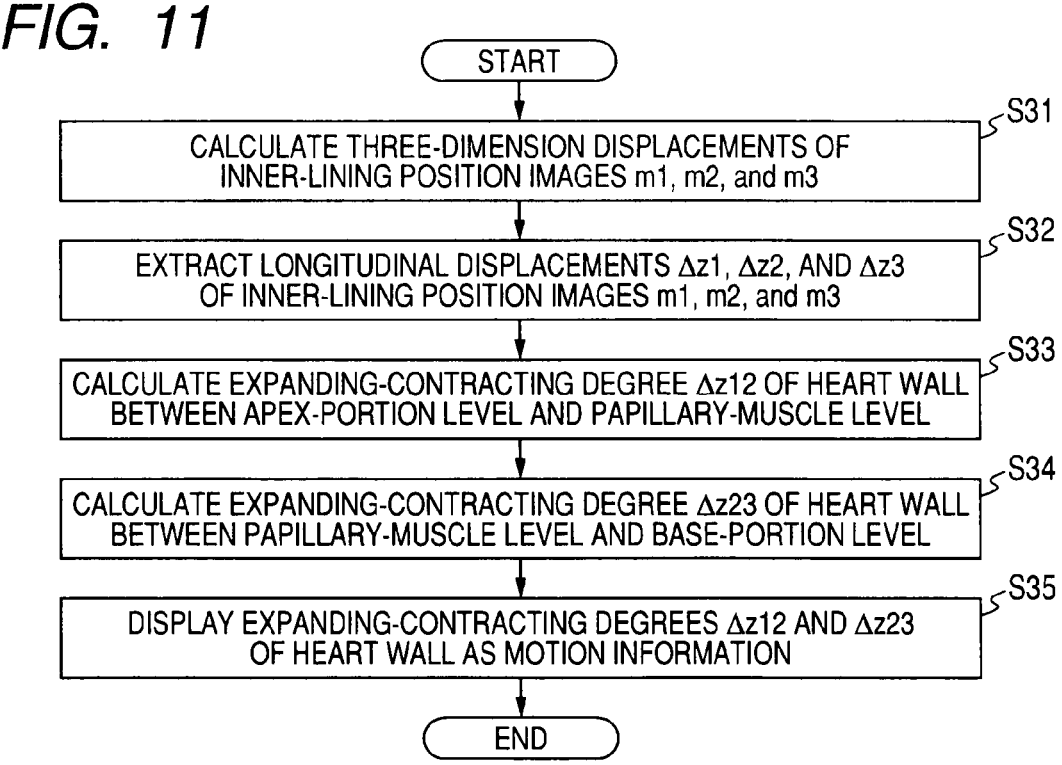
FIG. 11 is a flowchart showing an example of the process of the ultrasonic diagnostic apparatus according to the preferred embodiment of the invention.

A process of acquiring longitudinal expansion-contraction (shortening) of the heart wall as the motion information will be described with reference to FIGS. 11 and 12.

First, the displacement calculating part 61 executes the three-dimensional tracking, respectively, on the inner-lining position image m1 of the apex portion short-axis image G1, the inner-lining position image m2 of the papillary muscle short-axis image G2 and the inner-lining position image m3 of the base portion short-axis image G3, on the basis of the plurality of volume data in time series (S03), thereby calculating three-dimensional displacements ($\Delta$x1, $\Delta$y1, and $\Delta$z1), ($\Delta$x2, $\Delta$y2, and $\Delta$z2) and ($\Delta$x3, $\Delta$y3, and $\Delta$z3) of tomographic images in which the measurement image regions are designated for the inner-lining position image m1, the inner-lining position image m2 and the inner-lining position image m3, respectively (S31). The displacement corresponds to an example of the "local motion information." The displacement calculating part may calculate three-dimensional displacements of the outer-lining position images M1, M2 and M3 instead of the inner-lining position images m1, m2 and m3.

At this moment, for example, for each time phase, the displacement calculating part 61 calculates three-dimensional displacements of the inner-lining position images m1, m2 and m3 as three-dimensional displacements with respect to a reference time phase at which the inner-lining position image m1 etc. are inputted in Step S09. The displacement calculating part may sequentially calculate the three-dimensional displacements of the inner-lining position images m1, m2 and m3 in continuous frames.

Additionally, $\Delta$x and $\Delta$y denote displacements in the X direction (one side of the direction will be +X direction) and in the Y direction shown in FIGS. 2 and 3, respectively. A plane including the X direction and the Y direction is parallel to the sections of the apex portion short-axis image G1, the papillary muscle short-axis image G2, and the base portion short-axis image G3. Additionally, $\Delta$z denotes a displacement in the Z direction (for example, an apex-portion direction will be the $-$Z direction and a base-portion direction will be the +Z direction when viewed from the papillary-muscle level) orthogonal to the X direction and the Y direction. The Z direction is parallel to the longitudinal direction of the heart.

Additionally, the displacement calculating part 61 extracts the displacements $\Delta$z1, $\Delta$z2 and $\Delta$z3 in the Z direction (longitudinal direction) from the three-dimensional displacements ($\Delta$x1, $\Delta$y1, and $\Delta$z1), ($\Delta$x2, $\Delta$y2, and $\Delta$z2) and ($\Delta$x3, $\Delta$y3, and $\Delta$z3) (S32).

Here, it is assumed that the sections of the apex portion short-axis image G1 etc. are parallel to the XY plane. However, even when the sections of the apex portion short-axis image G1 etc. are not parallel to the xy plane, it is possible to easily calculate the displacement in the Z direction by projecting the three-dimensional displacement (vector) in the Z direction.

Figure 12:
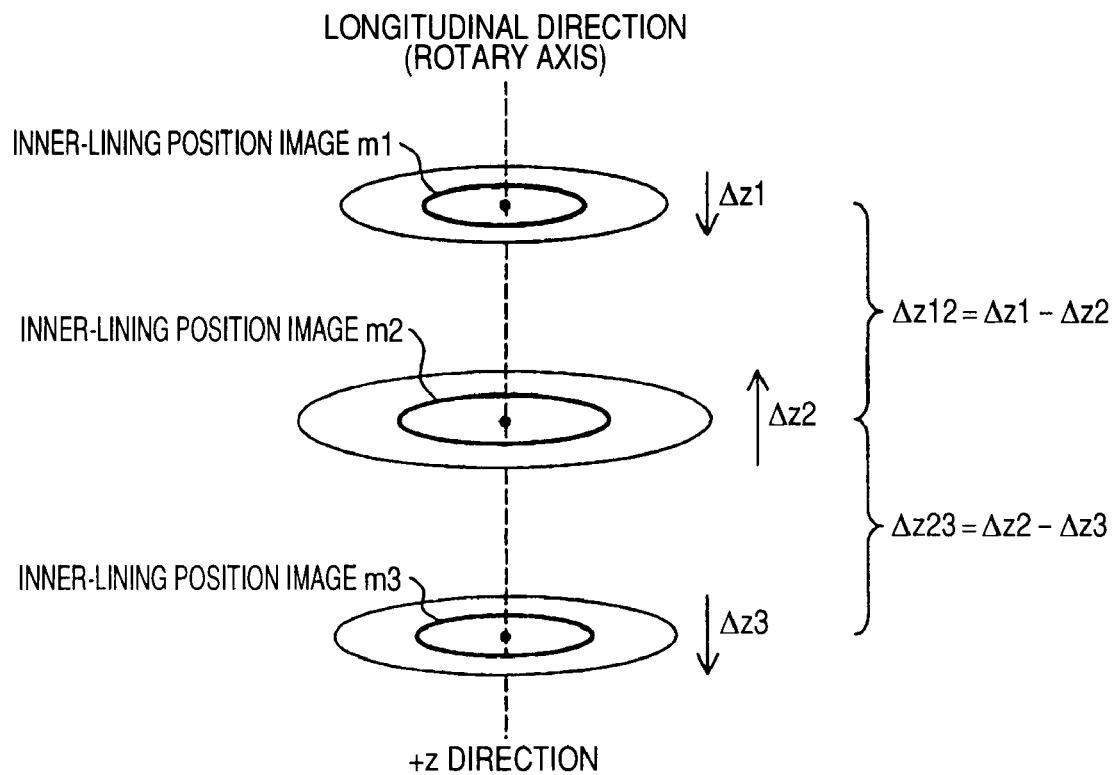
FIG. 12 is a schematic explanatory view showing the process of the ultrasonic diagnostic apparatus according to the preferred embodiment of the invention.

Next, as shown in FIG. 12, the motion information calculating part 62 calculates the difference between the displacement $\Delta$z1 of the inner-lining position image m1 in the Z direction and the displacement $\Delta$z2 of the inner-lining position image m2 in the Z direction to obtain the expansion-contraction $\Delta$z12=$\Delta$z1$-$$\Delta$z2 (or $\Delta$z2$-$$\Delta$z1) of the heart wall between the apex-portion level and the papillary-muscle level (S33). In the same manner, the motion information calculating part 62 calculates the difference between the displacement $\Delta$z2 of the inner-lining position image m2 in the Z direction and the displacement $\Delta$z3 of the inner-lining position image m3 in the Z direction to obtain the expansion-contraction $\Delta$z23=$\Delta$z2$-$$\Delta$z3 (or $\Delta$z3$-$$\Delta$z2) of the heart wall between the papillary-muscle level and the base-portion level (S34). The expansion-contraction $\Delta$z12 and $\Delta$z13 correspond to an example of "difference information."

The controller 9 controls the display part 81 to display the expansion-contraction $\Delta$z12 and $\Delta$z23 of the heart wall calculated in Steps S33 and S34 as the motion information showing the magnitude of the expansion-contraction of the heart wall (S35). The user can grasp the magnitude of the expansion-contraction of the heart wall by referring to the displayed expansion-contraction $\Delta$z12 and $\Delta$z23 of the heart wall.

It is also possible to calculate the expansion-contraction of the heart wall for each of the inner lining and the outer lining, respectively, and evaluate the magnitude of the expansion-contraction on the basis of the two values of the expansion and the contraction (for example, obtaining an average from the two values of the expansion-contraction).

Additionally, by differentiating the expansion-contraction $\Delta$z12 by time, it is possible to obtain the velocity of the expansion-contraction motion of the heart wall between the inner-lining position images m1 and m2. In the same manner, by differentiating the expansion-contraction $\Delta$z23 by time, it is possible to obtain the velocity of the expansion-contraction motion of the heart wall between the inner-lining position images m2 and m3. Then, it is possible to configure so as to display the velocities on the display part 81. Here, the "differentiation" has the same meaning as described above.

(Motion Information: Longitudinal Strain)

A process of acquiring a longitudinal strain of the heart wall as the motion information will be described with reference to FIGS. 13 and 14. The strain is information showing the degree of the strain magnitude of the heart wall, and represents the strain state of the heart wall.

First, in the same manner as in the case of obtaining the longitudinal expansion-contraction, the displacement calculating part 61 calculates the three-dimensional displacements ($\Delta$x1, $\Delta$y1, and $\Delta$z1), ($\Delta$x2, $\Delta$y2, and $\Delta$z2) and ($\Delta$x3, $\Delta$y3, and $\Delta$z3) of the tomographic images having the measurement image regions designated thereon for each of the inner-lining position image m1, the inner-lining position image m2 and the inner-lining position image m3 (S41), and extracts the displacements $\Delta$z1, $\Delta$z2 and $\Delta$z3 in the Z direction (longitudinal direction) from the three-dimensional displacements (S42).

Next, in the same manner as described above, the motion information calculating part 62 calculates the expansion-contraction $\Delta$z12=$\Delta$z1$-$$\Delta$z2 of the heart wall between the apex-portion level and the papillary-muscle level (S43), and calculates the expansion-contraction $\Delta$z23=$\Delta$z2$-$$\Delta$z3 of the heart wall between the papillary-muscle level and the base-portion level (S44).

Figure 9:
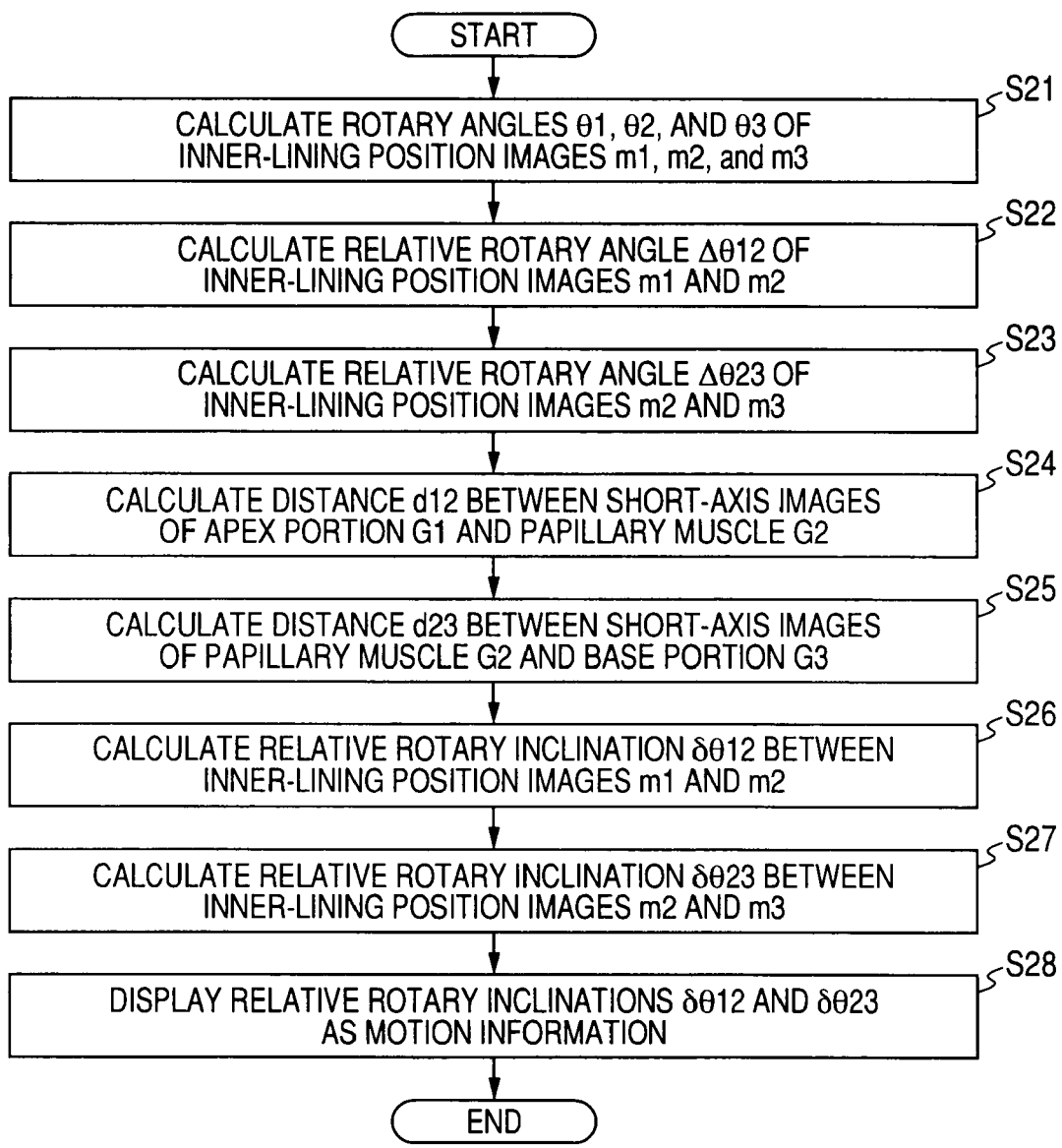
FIG. 9 is a flowchart showing an example of the process of the ultrasonic diagnostic apparatus according to the preferred embodiment of the invention.

In the same manner as in Steps S24 and S25 shown in FIG. 9, for the apex portion short-axis image G1, the papillary muscle short image G2 and the base portion short-axis image G3 in which the measurement image regions are designated, the motion information calculating part 62 calculates the distance d12 between the apex portion short-axis image G1 and the papillary muscle short-axis image G2 (S45), and calculates the distance d23 between the papillary muscle short-axis image G2 and the base portion short-axis image G3.

Furthermore, the motion information calculating part 62 divides the expansion-contraction $\Delta$z12 calculated in Step S43 by the distance d12 calculated in Step S45 to calculate the longitudinal strain $\delta$z12=$\Delta$z12/d12 between the apex-portion level and the papillary-muscle level (S47). Additionally, the motion information calculating part 62 divides the expansion-contraction $\Delta$z23 calculated in Step S44 by the distance d23 calculated in Step S46 to calculate the longitudinal strain $\delta z23 = \Delta z23/d23$ between the papillary-muscle level and the base-portion level (S48).

The controller 9 controls the display part 81 to display the strains $\delta z12$ and $\delta z23$ of the heart wall calculated in Step S47 and S48 as the motion information showing the magnitude of the strain of the heart wall (S49). The user can grasp the magnitude of the strain of the heart wall by referring to the displayed strains $\delta z12$ and $\delta z23$ of the heart wall.

It is also possible to calculate the strains of the inner lining of the heart wall and the outer lining of the heart wall, respectively, and evaluate the magnitude of the strain on the basis of the two strain values (for example, obtaining an average from the two strain values).

(Motion Information: Longitudinal Strain Rate)

A process of acquiring a longitudinal strain rate of the heart wall as the motion information will be described. The strain rate is information showing a variation rate with time of the strain of the heart wall, and represents the strain state of the heart wall.

Figure 13:
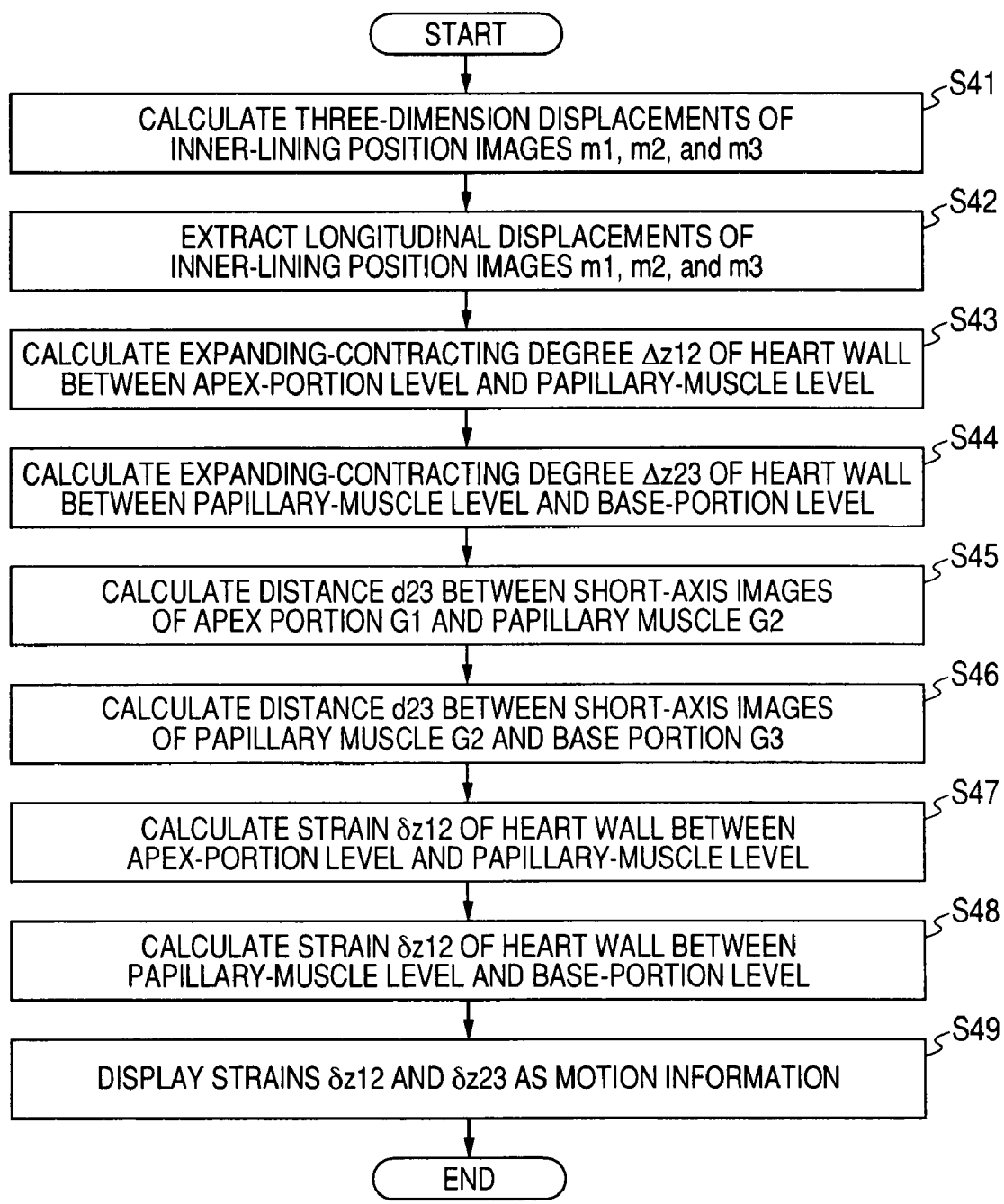
FIG. 13 is a flowchart showing an example of the process of the ultrasonic diagnostic apparatus according to the preferred embodiment of the invention.
Figure 14:
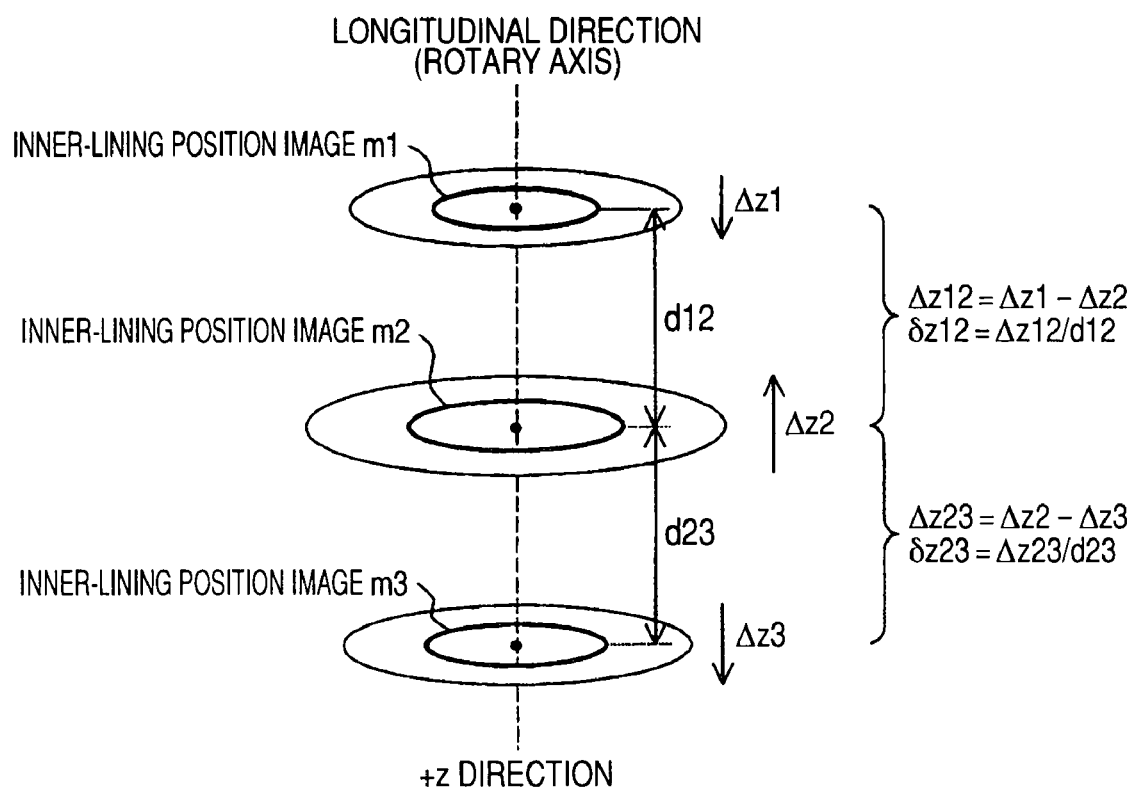
FIG. 14 is a schematic explanatory view showing the process of the ultrasonic diagnostic apparatus according to the preferred embodiment of the invention.

In the case of obtaining the strain rate, by performing the same processes in Steps S41 to S48 of the flowchart shown in FIG. 13, the longitudinal strain $\delta z12$ between the apex-portion level and the papillary-muscle level and the longitudinal strain $\delta z23$ between the papillary-muscle level and the base-portion level are calculated.

Here, the strain $\delta z12$ and the strain $\delta z23$ are calculated for the apex portion short-axis image G1, the papillary muscle short-axis image G2 and the base portion short-axis image G3 at two time phases t1 and t2 (t1≠t2). The motion information calculating part 62 divides the strain $\delta z12$ by the time interval $\Delta t = |t1 - t2|$ to calculate the longitudinal strain rate between the apex-portion level and the papillary-muscle level. Additionally, the motion information calculating part divides the $\delta z23$ by the time interval $\Delta t$ to calculate the longitudinal strain rate between the papillary-muscle level and the base-portion level. The motion information calculating part may perform the general differentiation calculation to calculate the strain rate from the strain.

The controller 9 controls the display part 81 to display the calculated strain rates $\delta z12/\Delta t$ and $\delta z23/\Delta t$ of the heart wall as the motion information showing the variation rate with time of the strain of the heart wall. The user can grasp the variation rate with time of the strain of the heart wall by referring to the displayed strain rate of the heart wall.

Additionally, it is also possible to calculate the strain rates of the inner lining and the outer lining of the heart wall, respectively, and evaluate the variation rate with time of the strain on the basis of the two values of the strain rates (for example, obtaining an average of the two values of the strain rates).

[Effects And Advantages]

According to the ultrasonic diagnostic apparatus 1 operating as described above, the following effects and advantages are produced.

The ultrasonic diagnostic apparatus 1 first creates image data of a moving picture at each of two or more sectional positions of a biological tissue (heart) (for example, three sectional positions of the apex-portion level, the papillary-muscle level and the base-portion level). The image data of the moving picture is image data of a series of tomographic images in time series. In real-time display of the image, there is a case where the moving picture cannot be displayed due to the operation velocity of the CPU or the like. In this case, for example, only the tomographic image can be displayed by performing the MPR process on the volume data.

Next, the ultrasonic diagnostic apparatus 1 displays one tomographic image of the series of tomographic images for each of the two or more sectional positions. The user designates the measurement image region on each of the displayed tomographic images by operating the operation part 82. When the measurement image region is designated, the ultrasonic diagnostic apparatus 1 calculates the displacement in time series of the designated measurement image regions on the tomographic images at the sectional positions. Then, on the basis of the displacement of the measurement image regions calculated for the two or more sectional positions, the ultrasonic diagnostic apparatus calculates the motion information showing the motion state of the biological tissue.

Thus, unlike the known method in which the motion of the biological tissue is measured in terms of the displacement (local motion information) of the measurement image region at one sectional position, the ultrasonic diagnostic apparatus 1 according to the invention designates the measurement image regions at two or more sectional positions and obtains the displacements (local motion information) of the two or more measurement image regions to acquire the motion information. Therefore, it is possible to measure the three-dimensional motion of the biological tissue.

To be specific, on the basis of the displacements of the measurement image regions at the sectional positions, the relative displacement at the different sectional positions (the relative displacement (difference information); the relative rotary angle, the expansion-contraction, and the like described above) is obtained, whereby it is possible to measure the three-dimensional motion of the biological tissue on the basis of the relative displacement. Additionally, as a result of execution of the measurement on the basis of such a relative displacement, it is not necessary to perform data analysis on a portion between the sectional positions (that is, it is not necessary to perform three-dimension data analysis). Therefore, there is a merit that the three-dimensional measurement can be executed in a short time.

Additionally, by three-dimensional tracking of the measurement image region designated on the two-dimensional tomographic image on the basis of the volume data, it is possible to obtain the three-dimensional displacement of the measurement image region, so that it is possible to perform the measurement with high precision.

If the two-dimensional tracking and the three-dimensional tracking are selectively carried out on the basis of the motion information to be acquired, it is possible to increase the efficiency in processing. In accordance with the motion information to be acquired, it is possible to configure the ultrasonic diagnostic apparatus capable of performing only the two-dimensional tracking or the ultrasonic diagnostic apparatus capable of performing only the three-dimensional tracking.

Additionally, according to the ultrasonic diagnostic apparatus 1, unlike the known configuration in which the measurement image region is designated on the displayed pseudo-three-dimensional image, the tomographic image (MPR image) based on the volume data is displayed and the measurement image region is designated on the tomographic image, so that it is possible to easily designate the measurement image region.

According to the ultrasonic diagnostic apparatus 1, other than the above-described motion information, for example, it is possible to acquire various (local) motion information, such as a variation (velocity) of the thickness of the heart wall, a strain or a strain rate of the heart wall in the thickness direction (short-axis direction), a rotary angle (rotary velocity) of the inner lining or the outer lining of the heart wall about the longitudinal direction, a strain or a strain rate of the heart wall in a rotary direction about the longitudinal direction, and a relative rotary angle of the inner lining or the outer lining of the heart wall in the rotary direction about the longitudinal direction. As conventional, it is possible to obtain the motion information by two-dimensional tracking on one tomographic image. Additionally, even when the three-dimensional tracking is used, for example, it is possible to acquire the motion information in terms of the image (image obtained by the rendering process) obtained by projecting the volume data in a predetermined line of a sight.

The variation of the thickness of the heart wall (the wall thickness) can be acquired by calculating the thickness of the heart wall for each of two tomographic images having different time phases and obtaining the difference therebetween. Here, the thickness of the heart wall can be obtained by obtaining a straight line orthogonal to a tangential line contacting the inner lining (or the outer lining) at an arbitrary position of the inner lining (or the outer lining), obtaining a position (intersection point) of the straight line intersecting the outer lining (or the inner lining), and then calculating a distance between the arbitrary position and the intersection point. Additionally, the variation velocity of the wall thickness can be easily obtained by dividing the variation of the wall thickness by the time between two tomographic images or by performing a general differentiation process (differentiation process having a variable of time) to the variation of the wall thickness.

It is possible to obtain the strain of the heart wall in the thickness direction by obtaining the variation of the wall thickness and dividing the variation of the wall thickness by the value of the wall thickness of one tomographic image (tomographic image at a certain time phase) of two tomographic images. It is possible to obtain the strain rate by dividing the strain value by the time interval between the time phases of the two tomographic images (or by differentiating the strain value by time).

It is possible to obtain the rotary angle of the inner lining (outer lining) of the heart wall about the longitudinal direction by obtaining the short-axis positions of the inner lining (outer lining) in the rotary direction for two tomographic images having different time phases, and calculating the position of the inner lining (outer lining) of one tomographic image with respect to the position of the inner lining (outer lining) of the other tomographic image. Additionally, it is possible to easily obtain the rotary velocity in the above-described manner.

The strain of the heart wall in the rotary direction about the longitudinal direction is obtained by calculating a distance between two positions of the inner lining (outer lining) in the rotary direction for each of two tomographic images having different time phases, and calculating a difference between the two distances, and dividing a value of the difference by the distance calculated for one of the two tomographic images. Additionally, it is possible to obtain the strain rate by dividing the strain value by the time interval between the time phases of two tomographic images.

It is possible to obtain the relative rotary angle of the inner lining and the outer lining of the heart wall in the longitudinal direction as the rotary direction, by obtaining the rotary angle of the inner lining and the rotary angle of the outer lining in two tomographic images having different time phases (described above), and calculating the difference therebetween.

Although a measurement image region parallel to the short-axis direction of the heart is designated in this embodiment, it is also possible to designate a measurement image region on a section parallel to the longitudinal direction. In this case, the straining motion and relative rotary gradient in the longitudinal direction can be obtained by two-dimensional tracking on a tomographic image in the relevant section. Additionally, the expansion-contraction, strain and strain rate in the short-axis direction can be obtained by executing three-dimensional tracking using volume data.

Furthermore, it is also possible to designate a measurement image region parallel to an arbitrary section of the heart. In this case, the motion information acquired from only a displacement in a direction parallel to the measurement image region can be obtained by two-dimensional tracking on a tomographic image in a direction parallel to the relevant section. Additionally, the motion information that needs a displacement in a direction orthogonal to the relevant section can be obtained by executing three-dimensional tracking using volume data.

Besides, even when executing three-dimensional ultrasonic scanning in an arbitrary scanning aspect for generating volume data, it is possible to execute a similar motion information acquiring process. For example, even when rotationally scanning a two-dimensional scanning plane, it is possible to execute a process as in the above-described embodiment. That is, it is possible to arbitrarily select an ultrasonic scanning aspect as far as volume data of a biological tissue can be created thereby.

[Modification]

The above-described ultrasonic diagnostic apparatus 1 is merely a preferred detailed example of the ultrasonic diagnostic apparatus according to the invention. Hereinafter, various modifications of the ultrasonic diagnostic apparatus according to the invention will be described.

[First Modification]

This modification is provided to facilitate an operation for designating a measurement image region on an image based on volume data obtained by executing three-dimension ultrasonic scan on a biological tissue. The ultrasonic diagnostic apparatus according to this modification has a configuration similar to that of the ultrasonic diagnostic apparatus 1 according to the above-described embodiment. Hereinafter, a process according to this modification will be described.

A process executed by the MPR processing part 52 of the image processor 5 before generation of image data of a series of tomographic images in time series is similar to that of the above-described embodiment. Although the respective image data of tomographic images at two or more sectional positions are generated in the above-described embodiment, the image data of a tomographic image only at one sectional position may be generated in this modification.

The controller 9 controls the display part 81 to display one tomographic image of the series of tomographic images. The user designates a measurement image region on the displayed tomographic image by operating the operation part 82. Accordingly, it is possible to more easily designate the measurement image region than in the known configuration in which a pseudo-three-dimensional image is displayed to designate the measurement image region.

According to this modification, for example, when designating the measurement image region parallel to the short-axis section of the heart, it is possible to calculate the variation (velocity) in thickness of the heart wall, the strain or strain rate of the heart wall in the thickness direction, the rotary angle (rotary velocity) of the inner lining or the outer lining of the heart wall about the longitudinal direction, the strain or strain rate of the heart wall in the rotary direction about the longitudinal direction, and the relative rotary angle of the inner lining or the outer lining of the heart wall in the rotary direction about the longitudinal direction.

[Second Modification]

The ultrasonic diagnostic apparatus 1 according to the above-described embodiment is configured such that the user operates the operation part 82 to designate the measurement image region. This modification is provided to automatically perform the measurement image region designating operation.

Figure 15:
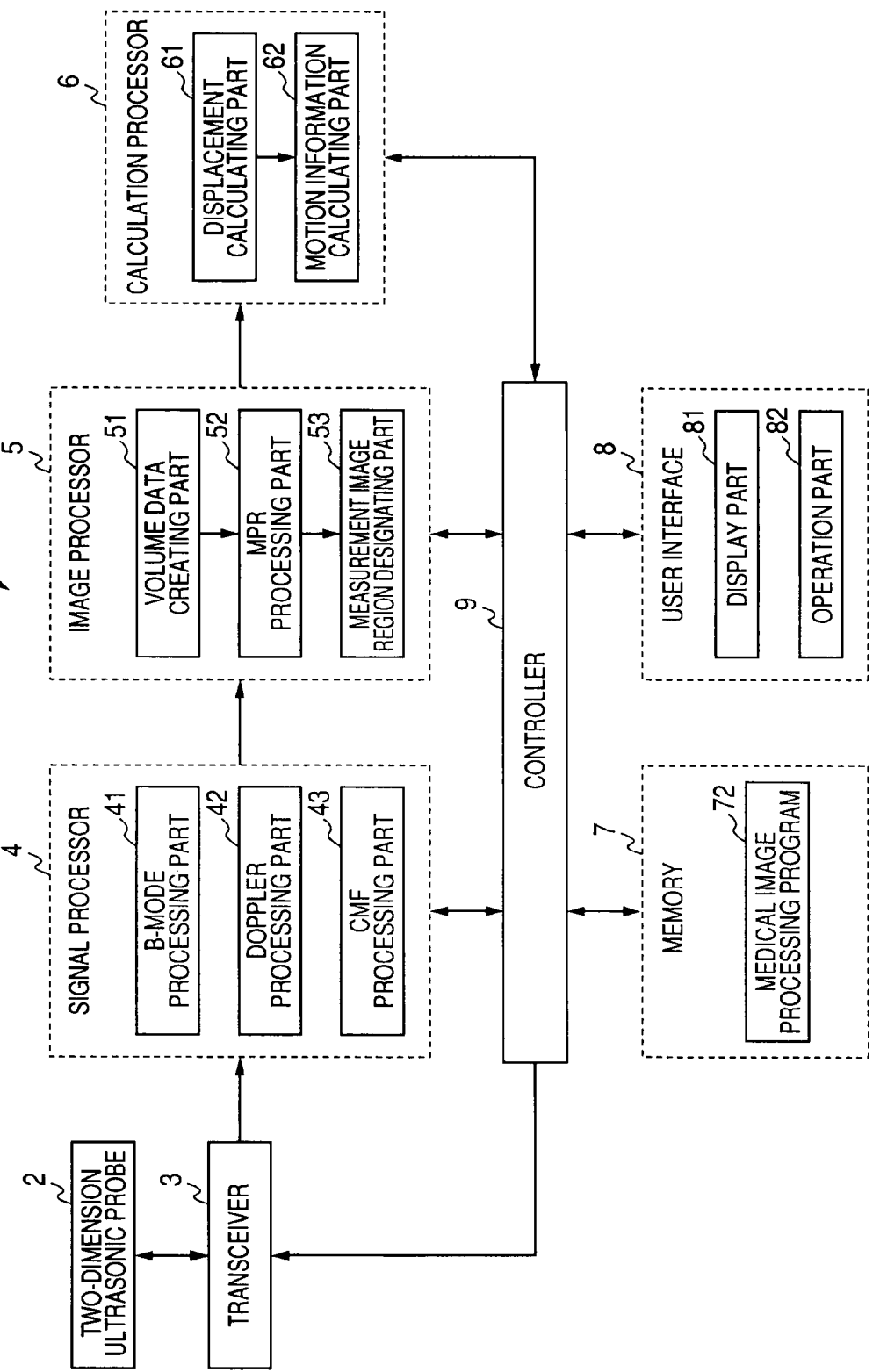
FIG. 15 is a schematic block diagram showing an example of an entire configuration in a modification of the ultrasonic diagnostic apparatus according to the preferred embodiment of the invention.

FIG. 15 shows an example of the ultrasonic diagnostic apparatus according to this modification. An ultrasonic diagnostic apparatus 100 shown in FIG. 15 has the substantially same configuration as the ultrasonic diagnostic apparatus 1 according to the above-described embodiment, but is different in that the image processor 5 is provided with a measurement image region designating part 53. Additionally, in order to perform the characteristic process of the modification, there is provided a medical image processing program 72 different from that of the above-described embodiment.

The measurement image region designating part 53 analyzes the image data of a tomographic image generated by the MPR processing part 52 (for example, the short-axis images of the apex portion, the papillary muscle, and the base portion), and designates the measurement image region on the tomographic image.

More specifically, the measurement image region designating part 53 applies, for example, a general boundary extraction process to analyze a pixel value of each pixel of the image data, thereby extracting a boundary portion of the biological tissue (e.g., the inner lining and the outer lining of the heart wall). Then, the measurement image region designating part 53 designates the extracted boundary portion as the measurement image region of the tomographic image. The measurement image region designating part 53 corresponds to an example of the "designating part" according to the invention, and includes a microprocessor that operates on the basis of, for example, the medical image processing program 72.

Figure 4:
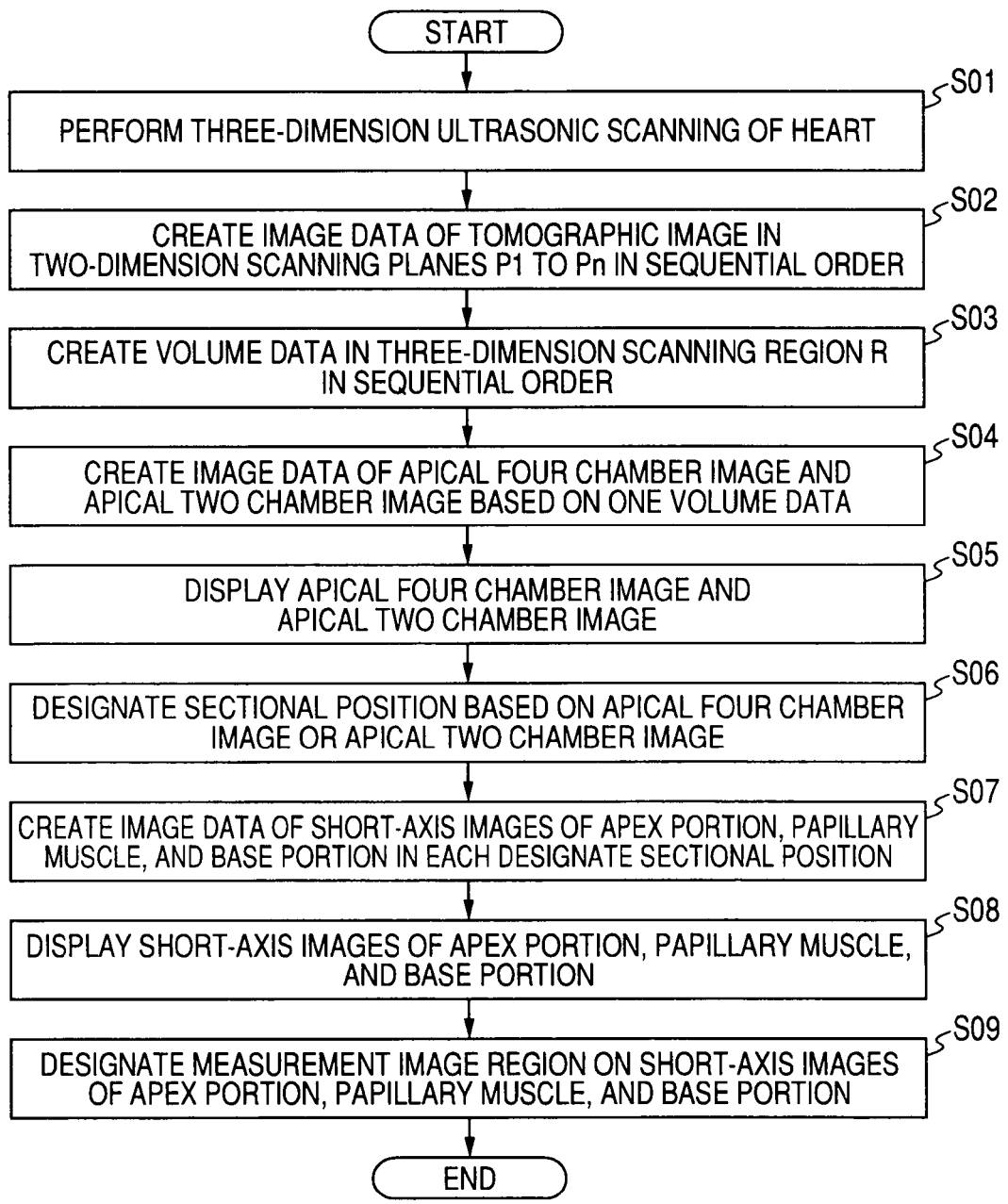
FIG. 4 is a flowchart showing an example of an operation aspect of the ultrasonic diagnostic apparatus according to the preferred embodiment of the invention.

A process carried out by the measurement image region designating part 53 corresponds to the procedure in Step S09 of the flowchart of FIG. 4. When the measurement image region designating part 53 performs the measurement image region designating process, the tomographic image may be displayed on the display part 81, or may be not displayed thereon.

Additionally, in order that the user can check the automatically designated measurement image region, it is desirable to display the tomographic image with the measurement image region inputted, on the display part 81. At this moment, it is desirable to configure such that the measurement image region can be appropriately changed by using the operation part 82.

Since the measurement image region is automatically designated in the configuration according to this modification, it is possible to easily designate the measurement image region (in fact, it is not necessary to perform the measurement image region designating operation when using the automatically designated measurement image region as it is).

[Third Modification]

In the ultrasonic diagnostic apparatus 1 according to the above-described embodiment, the three-dimension ultrasonic scanning operation is electronically carried out by using a two-dimension ultrasonic transducer in which the ultrasonic transducers are arranged two-dimensionally. This modification relates to an ultrasonic diagnostic apparatus in which an ultrasonic transducer is equipped with a one-dimension ultrasonic probe arranged in the one-dimension direction.

When using the one-dimension ultrasonic probe, the ultrasonic scanning operation is electronically carried out only in the one-dimension direction (the primary-scanning direction X shown in FIGS. 2 and 3). Therefore, the scanning operation is manually or mechanically carried out in the sub-scanning direction Y at the time of the three-dimension ultrasonic scanning operation.

Even if using such a one-dimension ultrasonic probe, it is possible to configure to generate volume data based on the three-dimension ultrasonic scanning operation, generate image data of a tomographic image based on the volume data, display the tomographic image and designate the measurement image region.

[Fourth Modification]

The ultrasonic diagnostic apparatus 1 according to the above-described embodiment calculates a displacement in time series of a measurement image region designated on a tomographic image at two or more sectional positions such as the apex-portion level and the papillary-muscle level, and calculates the motion information of a biological tissue on the basis of the displacement of the measurement image region at the two or more sectional positions. That is, in the above-described embodiment, the motion information is calculated on the basis of only the displacement of the designated measurement image region.

This modification is provided to automatically and additionally designate a measurement image region other than the designated measurement image region and to calculate the motion information by including the displacement of the automatically designated measurement image region. Hereinafter, the ultrasonic diagnostic apparatus according to this modification will be described. In the same manner as the ultrasonic diagnostic apparatus 100 shown in FIG. 15, the ultrasonic diagnostic apparatus according to this embodiment includes the measurement image region designating part 53.

An operation of the ultrasonic diagnostic apparatus according to this modification will be described. In the same manner as in the above-described embodiment, as the measurement image regions of the apex portion short-axis images G1, the papillary muscle G2 and the base portion G3 displayed on the display part 81, the user designates, for example, the inner-lining position images m1, m2 and m3 and the outer-lining position images M1, M2 and M3 (see FIGS. 5 and 6). The measurement image region may be designated by the automatic designating process according to the second modification.

Figure 16:
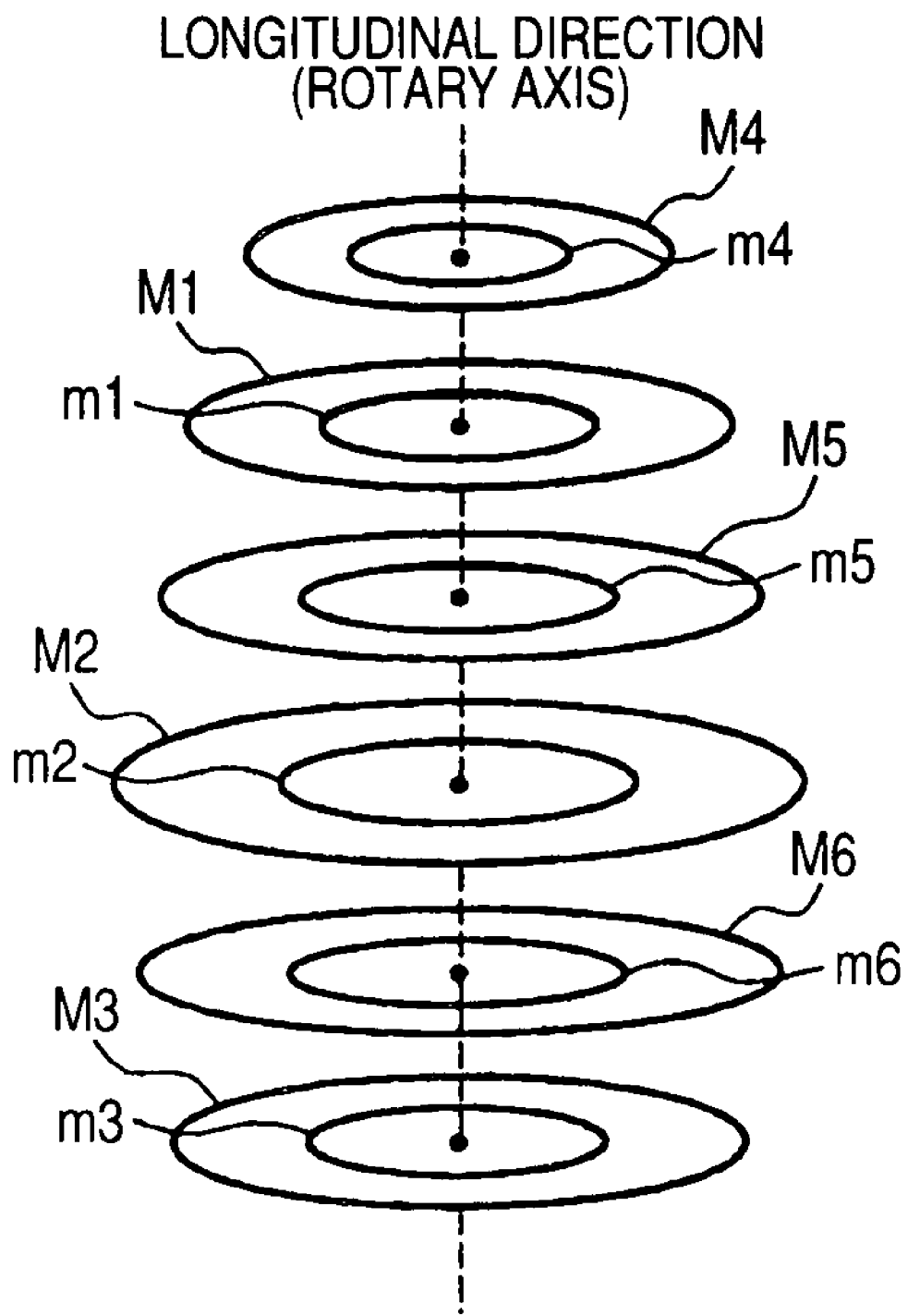
FIG. 16 is a schematic explanatory view showing a process of the modification of the ultrasonic diagnostic apparatus according to the preferred embodiment of the invention.

The measurement image region designating part 53 designates a measurement image region other than the designated measurement image regions m1 to m3 and M1 to M3. For example, as shown in FIG. 16, the measurement image region designating part 53 designates the inner-lining position image m4 and the outer-lining position image M4 at a position outside the apex portion short-axis image G1, designates the inner-lining position image m5 and the outer-lining position image M5 at a position between the apex portion short-axis image G1 and the papillary muscle short-axis image G2, and designates the inner-lining position image m6 and the outer-lining position image M6 at a position between the papillary muscle short-axis image G2 and the base portion short-axis image G3.

The measurement image region designating process will be described in more detail. The measurement image region designating part 53 first determines a sectional position (coordinate) for designating a new measurement image region, on the basis of the sectional positions (coordinates) of the apex portion short-axis image G1, the papillary muscle short-axis image G2, and the base portion short-axis image G3 in which the measurement image region is designated by the user or the like. This process is carried out, for example, in such a manner that a coordinate (a first Z coordinate) of a position away from the apex portion short-axis image G1 by a predetermined distance in a direction opposite to the papillary muscle short-axis image G2 is obtained, a coordinate (a second Z coordinate) at the center of the sections based on the Z coordinate of the apex portion short-axis image G1 and the Z coordinate of the papillary muscle short-axis image G2 is obtained, and then a coordinate (a third Z coordinate) at the center of the Z coordinate of the papillary muscle short-axis image G2 and the Z coordinate of the base portion short-axis image G3 is obtained Subsequently, the MPR processing part 52 creates the image data of the tomographic images parallel to the apex portion short-axis image G1 and the like at the first to third Z coordinates on the basis of the volume data.

The measurement image region designating part 53 analyzes a pixel value of the image data of the tomographic image at the first Z coordinate to extract the boundary portion of the heart wall, whereby the inside boundary portion is designated as the inner-lining position image m4 and the outside boundary portion is designated as the outer-lining position image M4. In the same manner, the measurement image region designating part analyzes a pixel value of the image data of the tomographic image at the second Z coordinate to extract the boundary portion of the heart wall, whereby the inside boundary portion is designated as the inner-lining position image m5 and the outside boundary portion is designated as the outer-lining position image M5. The measurement image region designating part analyzes a pixel value of the image data of the tomographic image at the third Z coordinate to extract the boundary portion of the heart wall, whereby the inside boundary portion is designated as the inner-lining position image m6 and the outside boundary portion is designated as the outer-lining position image M6. Then, the inner-lining position images m4 to m6 and the outer-lining position images M4 to M6 are respectively designated as new measurement image regions.

The displacement calculating part 61 according to this modification executes calculation of displacements in time series, respectively, on the measurement image regions m1 to m3 and M1 to M3 designated by the user, etc. and the measurement image regions m4 to m6 and M4 to M6 designated by the measurement image region designating part 53.

The motion information calculating part 62 calculates the motion information on the basis of all the displacements of the measurement image regions m1 to m6 and M1 to M6. For example, when evaluating the straining motion of the heart wall, the motion information calculating part calculates the relative rotary angle of the inner-lining position image m4 and the inner-lining position image m1, the relative rotary angle of the inner-lining position image m1 and the inner-lining position image m5, the relative rotary angle of the inner-lining position image m5 and the inner lining image m2, the relative rotary angle of the inner-lining position image m2 and the inner-lining position image m6, and the relative rotary angle of the inner-lining position image m6 and the inner-lining position image m3. In the same manner, the motion information calculating part is capable of calculating the relative rotary angles of the outer-lining position images M1 to M6.

The controller 9 controls the display part 81 to display the motion information based on the calculated relative rotary angle. Likewise, according to this modification, it is possible to obtain more accurate motion information than that of the above-described embodiment.

[Fifth Modification]

In the above-described embodiment, the sectional position for designating the measurement image region is designated by the user (see the sectional-position designating cursors C1 to C3 shown in FIG. 5). However, it is possible to configure to automatically designate the sectional position.

For example, like an observation before and after an operation or a progress observation, when there is the image data of the ultrasonic image for the same past biological tissue, the designated sectional position is memorized and the information at the past designated sectional position is read out, whereby it is possible to automatically designate the current sectional position.

Additionally, it is possible to previously set a typical sectional position such as the apex-portion level, the papillary-muscle level, and the base-portion level and to determine the typical sectional position on the basis of, for example, the volume data or the image data of the B-mode image.

Additionally, it is possible to configure such that the size of the biological tissue (for example, the longitudinal length of the heart) is analyzed on the basis of the image data or the like of the B-mode image and each sectional position upon dividing the size into a plurality of portions is designated as the sectional position for designating the measurement image region.

[Others]

In the above-described embodiment, the displacement of the biological tissue is obtained and the velocity is obtained by differentiating the displacement (dividing by a time interval). However, it is possible to configure such that the velocity is first obtained and the displacement is obtained by integrating the velocity.

Additionally, in the above-described embodiment, the motion information showing the (broader) motion state of the biological tissue is obtained and displayed, it is possible to configure such that the local motion information for each measurement image region is displayed. In this case, when the motion information is not calculated or displayed, it is possible to apply the ultrasonic diagnostic apparatus having a configuration necessary for calculating and displaying the local motion information (the same applies to a medical image processing apparatus and a medical image processing program described below).

<Second Embodiment>

A medical image processing apparatus according to the invention will be described. The medical image processing apparatus includes, for example, a computer connected to the ultrasonic diagnostic apparatus, and a computer connected to a database such as a PACS (Picture Archiving and Communication System) for storing the image data of the ultrasonic image. FIG. 17 shows an example of the medical image processing apparatus according to the invention. In FIG. 17, the same reference numerals are given to the same components as those of the first embodiment.

A medical image processing apparatus 1000 shown in FIG. 17 includes the image processor 5, the calculation processor 6, the memory 7, the user interface 8 and the controller 9, which are the same as those of the ultrasonic diagnostic apparatus 1 shown in FIG. 1. The memory 7 serves as an example of the "memory" according to the invention. The medical image processing apparatus 1000 is connected to an ultrasonic diagnostic apparatus 2000 and a medical image database 3000 via a network N such as a LAN (Local Area Network). The controller 9 according to this embodiment includes a network adaptor for performing data communication via the network N.

An operation of the medical image processing apparatus 1000 will be described. The image data of the ultrasonic image is inputted from the ultrasonic diagnostic apparatus 2000 or the medical image database 3000 to the medical image processing apparatus 1000.

When the inputted image data is the image data of a B-mode image, the volume-data creating part 51 creates volume data based on the image data. In the same manner as in the first embodiment, the MPR processing part 52 creates the image data of a series of tomographic images in time series on the basis of the volume data. The image data of the series of tomographic images is stored in the memory 7.

Additionally, when the inputted image data is volume data, the MPR processing part 52 creates the image data of a series of tomographic images in time series on the basis of the volume data. The image data of the series of tomographic images is stored in the memory 7.

The medical image processing apparatus 1000 executes the same process as in the first embodiment on the basis of the image data (and the volume data) of the series of tomographic images stored in the memory 7 (see FIGS. 4 to 14). Consequently, it is possible to measure the three-dimensional motion of a biological tissue in a short time. Additionally, it is possible to easily designate a region to measure the biological tissue.

As a modification of this embodiment, it is possible to employ a configuration in which the image processor 5 is provided with the measurement image region designating part 53 (see FIG. 15, a process based on the medical image processing program 72). Consequently, it is possible to execute the same process as in the second modification and fourth modification of the first embodiment.

<Third Embodiment>

A medical image processing program according to the invention will be described. The medical image processing programs 71 and 72 described in the first and second embodiments are an example of the medical image processing program according to the invention. The medical image processing program is for making a computer execute the processes described in the first embodiment and the modifications thereof. The medical image processing program may be stored in advance in a memory device such as a hard disk drive embedded in the computer, or may be stored in advance in a server on a network such as a LAN so that the computer reads out and executes the program.

It is possible to store the medical image processing program in an arbitrary storing medium so as to be readable by the computer. An example of the storing medium includes, for example, an optical disk, a magnet-optical disk (CD-ROM, DVD-RAM, DVD-ROM, MO, etc.), a magnetic storing medium (hard disk, floppy (trademark) disk, ZIP, etc.), and a semiconductor memory.

The invention claimed is:

1. An ultrasonic diagnostic apparatus, comprising:
an ultrasonic probe;
a transceiver configured to transmit and receive an ultrasonic wave to and from the ultrasonic probe;
an image creating part configured to create image data of a series of tomographic images in time series for each of two or more sectional positions of a biological tissue on the basis of a received signal obtained as a result of transmitting and receiving the ultrasonic wave;
a display part configured to display one tomographic image from among the series of tomographic images on the basis of the image data created for each of the two or more sectional positions;
a designating part configured to designate a measurement image region on the one displayed tomographic image for each of the two or more sectional positions; and
a calculator configured to calculate local motion information showing a motion state of the biological tissue in the designated measurement image region on the basis of the image data of the series of tomographic images for each of the two or more sectional positions, and configured to calculate motion information showing the motion state of the biological tissue on the basis of the local motion information calculated for each of the two or more sectional positions, wherein
the local motion information indicates a time series displacement of the one tomographic image in a same measurement image region,
the motion information indicates a difference of the local motion information between the two or more sectional positions, which are different sectional positions relating to different cross sections of the biological tissue, and
the display part displays the motion information calculated by the calculator.

2. The ultrasonic diagnostic apparatus according to claim 1:
wherein with the transceiver, the ultrasonic probe scans each of a plurality of positions along a predetermined direction, in an ultrasonic wave transmitting and receiving direction along a direction orthogonal to the predetermined direction, and repeats an ultrasonic wave transmitting and receiving operation along the predetermined direction and the orthogonal direction;
wherein the image creating part includes:
a first tomographic image creating part configured to create image data of a first tomographic image in a section of the biological tissue including the transmitting and receiving direction and the orthogonal direction, on the basis of received signals sequentially obtained at the time of scan in the ultrasonic wave transmitting and receiving direction of the orthogonal direction;
a volume data creating part configured to create volume data of the biological tissue, on the basis of the image data of the first tomographic image created for each of the plurality of positions; and
a second tomographic image creating part configured to create image data of a second tomographic image for each of the two or more sectional positions, on the basis of the created volume data; and
wherein a plurality of the image data of the second tomographic image obtained by repeating the ultrasonic wave transmitting and receiving operation for each of the two or more sectional positions are used as the image data of the series of tomographic images in time series.

3. The ultrasonic diagnostic apparatus according to claim 2, wherein the calculator calculates the local motion information showing a three-dimensional motion state of the biological tissue in the measurement image region designated by the designating part on the basis of the volume data for each of the two or more sectional positions, and calculates the motion information on the basis of the local motion information showing the three-dimensional motion state calculated for each of the two or more sectional positions.

4. The ultrasonic diagnostic apparatus according to claim 3, wherein the calculator obtains the motion information by calculating difference information showing a difference of the local motion information showing the three-dimensional motion state at two sectional positions among the two or more sectional positions.

5. The ultrasonic diagnostic apparatus according to claim 4, wherein:

sections of the series of tomographic images at one sectional position of the two sectional positions are parallel to sections of the series of tomographic images at the other sectional position; and the calculator calculates displacements in a direction orthogonal to the sections of the series of tomographic images of the biological tissue in the measurement image region on the basis of the local motion information showing the calculated three-dimensional motion state for the respective two sectional positions, and calculates, as the difference information, a difference between the displacements in the orthogonal direction calculated for the respective two sectional positions, thereby using the calculated difference between the displacements as the motion information showing an expanding and contracting motion of the biological tissue in the orthogonal direction.

6. The ultrasonic diagnostic apparatus according to claim 4, wherein:

sections of the series of tomographic images at one sectional position of the two sectional positions are parallel to sections of the series of tomographic images at the other sectional position; and the calculator calculates displacements in a direction orthogonal to the sections of the series of tomographic images of the biological tissue in the measurement image region on the basis of the local motion information showing the three-dimensional motion state calculated for the respective two sectional positions, and calculates, as the difference information, a difference between the displacements in the orthogonal direction calculated for the respective two sectional positions to differentiate the calculated difference between the displacements by time, thereby calculating the motion information showing a velocity of an expanding and contracting motion of the biological tissue in the orthogonal direction.

7. The ultrasonic diagnostic apparatus according to claim 4, wherein:

sections of the series of tomographic images at one sectional position of the two sectional positions are parallel to sections of the series of tomographic images at the other sectional position; and the calculator calculates displacements in a direction orthogonal to the sections of the series of tomographic images of the biological tissue in the measurement image region on the basis of the local motion information showing the calculated three-dimensional motion state for the respective two sectional positions, and calculates, as the difference information, a difference between the displacements in the orthogonal direction calculated for the respective two sectional positions to divide the calculated difference of the displacements by an original distance between the two sectional positions, thereby using a quotient as the motion information showing a strain of the biological tissue in the orthogonal direction.

8. The ultrasonic diagnostic apparatus according to claim 4, wherein:

sections of the series of tomographic images at one sectional position of the two sectional positions are parallel to sections of the series of tomographic images at the other sectional position; and the calculator calculates displacements in a direction orthogonal to the sections of the series of tomographic images of the biological tissue in the measurement image region on the basis of the local motion information showing the calculated three-dimensional motion state for the respective two sectional positions, and calculates a difference, as the difference information, between the displacements in the orthogonal direction calculated for the respective two sectional positions to divide the calculated difference of the displacements by an original distance between the two sectional positions and differentiate a quotient by time, thereby calculating the motion information showing a strain rate of the biological tissue in the orthogonal direction.

9. The ultrasonic diagnostic apparatus according to claim 1, wherein the calculator obtains the motion information by calculating difference information showing a difference of the local motion information at two sectional positions among the two or more sectional positions.

10. The ultrasonic diagnostic apparatus according to claim 9; wherein sections of the series of tomographic images at one sectional position of the two sectional positions are parallel to sections of the series of tomographic images at the other sectional position; and the calculator calculates, as the local motion information, a rotary angle of the biological tissue in the measurement image region about a direction orthogonal to the sections of the series of tomographic images, for each of the two sectional positions, and calculates, as the difference information, a difference between the rotary angles calculated for the two sectional positions, thereby using the calculated difference between the rotary angles as the motion information showing a straining motion of the biological tissue.

11. The ultrasonic diagnostic apparatus according to claim 9, wherein:

sections of the series of tomographic images at one sectional position of the two sectional positions are parallel to sections of the series of tomographic images at the other sectional position; and the calculator calculates, as the local motion information, a rotary angle of the biological tissue in the measurement image region about a direction orthogonal to the sections of the series of tomographic images for each of the two sectional positions, and calculates, as the difference information, a difference between the rotary angles calculated for the two sectional positions to differentiate the calculated difference between the rotary angles by time, thereby calculating the motion information showing a velocity of a straining motion of the biological tissue.

12. The ultrasonic diagnostic apparatus according to claim 9, wherein:

sections of the series of tomographic images at one sectional position of the two sectional positions are parallel to sections of the series of tomographic images at the other sectional position; and the calculator calculates, as the local motion information, a rotary angle of the biological tissue in the measurement image region about a direction orthogonal to the sections of the series of tomographic images for each of the two sectional positions, and calculates, as the difference information, a difference between the rotary angles calculated for the two sectional positions to divide the calculated difference between the rotary angles by a distance between the two sectional positions, thereby obtaining the motion information showing a relative rotary gradient of the biological tissue.

13. The ultrasonic diagnostic apparatus according to claim 1, wherein:

the designating part includes an automatic designating part configured to designate a new measurement image region at a sectional position different from the two or more sectional positions on the basis of the measurement image region designated on the one tomographic image displayed by the display part; and the calculator calculates the local motion information showing the motion state of the biological tissue in the new designated measurement image region, and calculates the motion information on the basis of the local motion information calculated for each of the two or more sectional positions and the different sectional position.

14. The ultrasonic diagnostic apparatus according to claim 1, wherein:
the biological tissue is a heart; and
the measurement image region designated by the designating part is an image region corresponding to a heart wall of the heart in the one tomographic image displayed by the display part.

15. The ultrasonic diagnostic apparatus according to claim 1, wherein the calculator designates a plurality of measurement points in the measurement image region designated on the one displayed tomographic image, obtains positions of the plurality of measurement points in each of the series of tomographic images, calculates a displacement in time series or a displacement velocity of each of the plurality of measurement points on the basis of the obtained positions, and calculates a displacement of the measurement image region on the basis of the displacement or the displacement velocity calculated for each of the plurality of measurement points.

16. The ultrasonic diagnostic apparatus according to claim 1, wherein:
the ultrasonic probe includes a plurality of ultrasonic transducers arranged two-dimensionally: and
the transceiver controls the plurality of ultrasonic transducers individually or by group of two or more so as to scan with an ultrasonic wave in a predetermined direction and a direction orthogonal to the predetermined direction.

17. The ultrasonic diagnostic apparatus according to claim 1, wherein the two or more sectional positions are displaced relative to one another in a longitudinal direction relating to a rotary axis of the biological tissue.

18. A medical image processing apparatus configured to process image data of a medical image of a biological tissue obtained by an ultrasonic diagnostic apparatus, the medical image processing apparatus comprising:
a memory configured to store image data of a series of tomographic images in time series at two or more sectional positions of a biological tissue;
a display part configured to display one tomographic image from among the series of tomographic images on the basis of the stored image data for the respective two or more sectional positions;
a designating part configured to designate a measurement image region on the displayed one tomographic image for each of the two or more sectional positions; and
a calculator configured to calculate local motion information showing a motion state of the biological tissue in the designated measurement image region on the basis of the image data of the series of tomographic images for each of the two or more sectional positions, and configured to calculate motion information showing the motion state of the biological tissue on the basis of the local motion information calculated for each of the two or more sectional positions, wherein
the local motion information indicates a time series displacement of the one tomographic image in a same measurement image region,
the motion information indicates a difference of the local motion information between the two or more sectional positions, which are different sectional positions relating to different cross sections of the biological tissue, and
the display part displays the motion information calculated by the calculator.

19. A medical image processing program for causing a computer having a memory configured to store image data of a series of tomographic images in time series at each of two or more sectional positions of a biological tissue and a display part to execute the functions of:
displaying one tomographic image from among the series of tomographic images on the display on the basis of the stored image data for each of the two or more sectional positions;
in response to designation of a measurement region on the one displayed tomographic image, calculating local motion information showing a motion state of the biological tissue in the designated measurement image region on the basis of the image data of the series of tomographic images for each of the two or more sectional positions, the local motion information indicating a time series displacement of the one tomographic image in a same measurement image region;
calculating motion information showing a motion state of the biological tissue on the basis of the local motion information calculated for each of the two or more sectional positions, the motion information indicating a difference of the local motion information between the two or more sectional positions, which are different sectional positions relating to different cross sections of the biological tissue; and
displaying the calculated motion information on the display.

* * * * *